US012793826B2

(12) United States Patent
Ahmed et al.

(10) Patent No.: US 12,793,826 B2
(45) Date of Patent: Nov. 10, 2026

(54) IMAGING TRAY FOR USE WITH A SYSTEM FOR IMAGING PHARMACY WORKFLOW IN A VIRTUAL VERIFICATION SYSTEM

(71) Applicant: CVS Pharmacy, Inc., Woonsocket, RI (US)

(72) Inventors: Mohammed M. Ahmed, Chicago, IL (US); Jeffrey M. Bragg, Cumberland, RI (US); David Fafel, Nashua, NH (US); Shilanna N. Gallo, Littleton, MA (US); Thomas J. Maresca, Saunderstown, RI (US); Steven J. Mergner, Coventry, RI (US); Vanteya A. Pandit, North Attleboro, MA (US); Grant Peret, Bedford, NH (US); Kyle Robertson, Manchester, NH (US)

(73) Assignee: CVS Pharmacy, Inc., Woonsocket, RI (US)

( * ) Notice: Subject to any disclaimer, the term of this patent is extended or adjusted under 35 U.S.C. 154(b) by 186 days.

(21) Appl. No.: 18/667,179

(22) Filed: May 17, 2024

(65) Prior Publication Data

US 2024/0304295 A1 Sep. 12, 2024

Related U.S. Application Data

(63) Continuation of application No. 17/330,803, filed on May 26, 2021, now Pat. No. 12,027,247.

(Continued)

(51) Int. Cl.

*A61J 7/02* (2006.01)
*A61J 1/03* (2023.01)

(Continued)

(52) U.S. Cl.

CPC ............ *G16H 20/13* (2018.01); *A61J 7/0069* (2013.01); *A61J 7/02* (2013.01); *G06Q 30/018* (2013.01);

(Continued)

(58) Field of Classification Search

CPC . G16H 20/13; A61J 7/0069; A61J 7/02; A61J 1/03; G06Q 30/018; G06T 7/0004;

(Continued)

(56) References Cited

U.S. PATENT DOCUMENTS

| | | | |
|---|---|---|---|
| D193,487 | S | 8/1962 | Levenhagen |
| D228,156 | S | 8/1973 | Antaya |

(Continued)

FOREIGN PATENT DOCUMENTS

| | | | |
|---|---|---|---|
| CN | 104777143 | A | 7/2015 |
| WO | 2012056317 | A2 | 5/2012 |

OTHER PUBLICATIONS

Palenychka et al., "Verification of Medication Dispensing Using the Attentive Computer Vision Approach," 2018 IEEE International Symposium on Circuits and Systems (ISCAS), Florence, Italy, 2018, pp. 1-4, doi: 10.1109/ISCAS.2018.8351202. ( Year: 2018).

(Continued)

*Primary Examiner* — Siamak Harandi
(74) *Attorney, Agent, or Firm* — Patent Law Works, LLP

(57) ABSTRACT

A method and system provide for automated counting of prescription product and enables virtual verification of the dispensed prescription product. The method and system include counting a quantity of pills of a prescription product on a first portion of a tray, retaining the quantity of pills after the counting in a second portion of the tray, receiving at least the second portion of the tray into an imaging device, and capturing, with a first camera, an image of the quantity of pills in the second portion of the tray.

21 Claims, 23 Drawing Sheets

Related U.S. Application Data

(60) Provisional application No. 63/032,328, filed on May 29, 2020.

(51) Int. Cl.
*A61J 7/00* (2006.01)
*G06Q 30/018* (2023.01)
*G06T 7/00* (2017.01)
*G16H 20/13* (2018.01)

(52) U.S. Cl.
CPC .......... *G06T 7/0004* (2013.01); *G06T 7/0012* (2013.01); *G06T 2207/30004* (2013.01); *G06T 2207/30242* (2013.01)

(58) Field of Classification Search
CPC ......... G06T 7/0012; G06T 2207/30004; G06T 2207/30242; G06T 7/12; G06T 7/62; G06T 2207/20081; G06T 2207/20084; G06T 7/001
See application file for complete search history.

(56) References Cited

U.S. PATENT DOCUMENTS

| | | | |
|---|---|---|---|
| D235,785 | S | 7/1975 | Collister et al. |
| D236,538 | S | 8/1975 | Adams |
| D243,259 | S | 2/1977 | Martin, Jr. et al. |
| D254,648 | S | 4/1980 | Rosselli |
| D262,507 | S | 1/1982 | Wooldridge |
| D266,301 | S | 9/1982 | Hall |
| D298,968 | S | 12/1988 | McAllister |
| D342,572 | S | 12/1993 | Lapsker et al. |
| 5,597,995 | A | 1/1997 | Williams |
| D430,399 | S | 9/2000 | Pawuk |
| 6,176,392 | B1 | 1/2001 | William |
| 6,535,637 | B1 | 3/2003 | Wootton |
| 6,691,058 | B2 | 2/2004 | Blakley |
| 6,738,723 | B2 | 5/2004 | Hamilton |
| 7,006,214 | B2 | 2/2006 | Rzasa |
| 7,058,584 | B2 | 6/2006 | Kosinski |
| 7,398,999 | B2 | 7/2008 | Kaufman |
| 7,668,618 | B2 | 2/2010 | Szesko |
| 7,702,525 | B2 | 4/2010 | Kosinski |
| 7,848,934 | B2 | 12/2010 | Kobylevsky |
| 7,860,724 | B2 | 12/2010 | Chudy |
| 7,995,831 | B2 | 8/2011 | Eller |
| 8,060,380 | B2 | 11/2011 | Sullivan |
| 8,136,332 | B2 | 3/2012 | Rice |
| 8,150,706 | B2 | 4/2012 | Kobylevsky |
| D662,218 | S | 6/2012 | Pittman |
| 8,224,483 | B1 | 7/2012 | Ansari |
| 8,244,587 | B2 | 8/2012 | Denny |
| 8,295,582 | B2 | 10/2012 | Eller |
| 8,417,539 | B2 | 4/2013 | Chapman |
| 8,543,411 | B2 | 9/2013 | Koster |
| 9,532,928 | B2 | 1/2017 | Devita et al. |
| D847,372 | S | 4/2019 | Crawford et al. |
| 10,593,336 | B2 | 3/2020 | Boyadjiev |
| 11,190,944 | B2 | 11/2021 | Shima |
| 11,232,698 | B1 | 1/2022 | Kurfirst |
| D950,952 | S | 5/2022 | Kennedy, III et al. |
| D954,992 | S | 6/2022 | Berka |
| 11,581,079 | B1 | 2/2023 | Jhaveri |
| 2004/0064215 | A1 | 4/2004 | Greeven |
| 2004/0138921 | A1 | 7/2004 | Broussard |
| 2004/0172289 | A1 | 9/2004 | Kozic |
| 2006/0124656 | A1 | 6/2006 | Popovich |
| 2007/0008523 | A1 | 1/2007 | Kaye |
| 2007/0047980 | A1 | 3/2007 | Limer |
| 2008/0059240 | A1 | 3/2008 | Potuluri |
| 2009/0030722 | A1 | 1/2009 | Wiener |
| 2009/0048863 | A1 | 2/2009 | Kozlowski |
| 2009/0048871 | A1 | 2/2009 | Skomra |
| 2009/0080735 | A1 | 3/2009 | Chapman |
| 2009/0285663 | A1 | 11/2009 | Chemel |
| 2010/0094653 | A1 | 4/2010 | Tribble |
| 2011/0122241 | A1 | 5/2011 | Wang |
| 2011/0184751 | A1 | 7/2011 | Holmes |
| 2012/0290619 | A1 | 11/2012 | Delise, Jr. |
| 2013/0018503 | A1 | 1/2013 | Carson |
| 2013/0120595 | A1 | 5/2013 | Roach |
| 2013/0141566 | A1 | 6/2013 | Lang |
| 2013/0142406 | A1 | 6/2013 | Lang |
| 2014/0156298 | A1 | 6/2014 | Crawford |
| 2014/0369555 | A1 | 12/2014 | Zhong |
| 2015/0261934 | A1 | 9/2015 | Miller |
| 2015/0302255 | A1 | 10/2015 | Gershtein |
| 2016/0026774 | A1 | 1/2016 | Joplin |
| 2016/0110518 | A1 | 4/2016 | Louie |
| 2016/0163034 | A1 | 6/2016 | Jacobs |
| 2016/0267357 | A1 | 9/2016 | Smith |
| 2017/0079885 | A1 | 3/2017 | Thompson |
| 2017/0132867 | A1 | 5/2017 | Berg |
| 2017/0264867 | A1 | 9/2017 | Amano |
| 2018/0225818 | A1 | 8/2018 | Jacobs |
| 2019/0034976 | A1 | 1/2019 | Hamedi |
| 2019/0096517 | A1 | 3/2019 | Reddy |
| 2019/0164281 | A1 | 5/2019 | Lewis |
| 2019/0287666 | A1 | 9/2019 | Qin |
| 2020/0156120 | A1 | 5/2020 | Amano |
| 2020/0402632 | A1 | 12/2020 | Van Schelven |
| 2020/0411158 | A1 | 12/2020 | Iwami |
| 2021/0035288 | A1 | 2/2021 | Liu |
| 2022/0270344 | A1 | 8/2022 | Darling |
| 2022/0301665 | A1 | 9/2022 | Shorten |
| 2025/0005899 | A1 | 1/2025 | Hamilton |

OTHER PUBLICATIONS

Laydig et al., "Systems and Methods for Determining Drug Potentcy Using Machine Learning Algorithm", pp. 1-37.

Zhang et al., "Raman spectroscopy and mapping technique for the identification of expired drugs," Spectrochimica Zeta Part A: Molecular and Biomolecular Spectroscopy, 224, Jul. 31, 2019, 9 pgs.

Assi et al., "Authentication of medicines using Raman spectroscopy," European Pharmaceutical Review, Issue 1, Feb. 16, 2011, available online at https://www.europeanpharmaceuticalreview.com/article/5609/authentication-of-medicines-using-raman-spectroscopy/, 16 pgs.

BEYOND3DPRINTS, Counting Box Funnel Tray for Pharmacists and Technicians, date unknown, available online, retrieved Oct. 18, 2022, from https://www.etsy.com/listing/1272432978/counting-box-funnel-tray-for-pharmacists?gpla=1&gao=1&&utm_source=google&utm_medium=cpc&utm_campaign=shopping_us_a-home_and_living-office-office_and_sc, 9 pgs.

Meruje, et al., "Monitoring of Medication Boxes Using Wireless Sensors", ProQuest LLC, (2021).

IMAGING TRAY FOR USE WITH A SYSTEM FOR IMAGING PHARMACY WORKFLOW IN A VIRTUAL VERIFICATION SYSTEM

FIELD OF THE INVENTION

The present disclosure relates to the filling and verification of prescriptions by a pharmacy. In particular, the present disclosure relates to virtual verification that a prescription has been filled correctly.

BACKGROUND OF THE DISCLOSURE

In today's pharmacy workflow, a number of steps require physical handling of the prescription product which is time consuming. For instance, a considerable amount of time is spent by pharmacy staff performing product verification in a prescription fulfillment workflow. The process of product verification may include the pharmacist having to open a vial, pour out the contents of the vial onto a tray, manually inspect and compare the contents against a stock image of a prescription product, pour contents back into the vial, close vial, place the vial in a bag, and so on.

SUMMARY

A method, system, and imaging tray provide for automated counting of prescription product and enable virtual verification of the dispensed prescription product.

In certain aspects, a tray comprises a first portion and a second portion. The first portion is for receiving a quantity of pills in a prescription. The first portion includes a first spout positioned on a periphery of the first portion for returning an excess amount of pills to a storage container. The second portion is for imaging the quantity of pills in the prescription. The second portion includes a second spout positioned on a periphery of the second portion. The second spout is configured for dispensing the quantity of pills into a sales container. The first portion and the second portion are connected so that the quantity of pills can be slid from the first portion to the second portion.

The second portion further includes an imaging area. The imaging area is configured to maintain a constant distance from an imaging device. In some implementations, the second portion includes at least one slope to bias the quantity of pills toward the imaging area. In some implementations, the second portion includes at least four slopes to bias the quantity of pills toward the imaging area.

In some implementations, the second portion is lower than the first portion while the tray is placed on a flat surface. In some implementations, the first portion and the second portion are divided by a physical barrier which allows the quantity of pills to be moved from the first portion to the second portion while preventing the quantity of pills from being moved from the second portion to the first portion.

The first portion of the imaging tray includes at least four sides. A first side and a second side of the at least four sides comprise two sidewall portions. The first and second sidewall portions are connected to the first spout. A third side of the at least four sides is connected to the second portion. A fourth side of the at least four sides is open to permit access to the first portion for sliding the quantity of pills from the first portion to the second portion. In some implementations, the second spout includes a top cap to assist in keeping the quantity of pills from spilling when the quantity of pills is being dispensed into the sales container. In some implementations, the second portion further comprises walls around the periphery of the second portion.

The imaging tray is configured to be inserted in an imaging device. When inserted in the imaging device, the first portion is disposed outside the imaging device, the second portion is disposed inside the imaging device, and the second portion is positioned in a field of view of a camera in the imaging device.

In certain aspects a tray includes a first portion, a second portion, and a physical barrier connecting the first portion and the second portion. The first portion is configured to manually receive a quantity of pills in a prescription. The first portion includes a first spout positioned on a periphery of the first portion and configured for returning an excess quantity of pills to a storage container. The second portion is configured to receive the quantity of pills from the first portion. The second portion comprises an imaging area configured to be in a field of view of a camera when the tray is inserted in an imaging device. The second portion includes a second spout positioned on the periphery of the second portion for dispensing the quantity of pills into a sales container. The physical barrier connecting the first portion and the second portion selectively allows the quantity of pills to be slid from the first portion to the second portion.

In some implementations, the second portion further comprises at least one slope to bias the quantity of pills toward the imaging area. In some implementations, the second portion includes at least four slopes to bias the quantity of pills toward the imaging area.

In some implementations, the physical barrier includes a step that positions the first portion higher than the second portion, and an opening at a top of the step to allow the quantity of pills to be moved from the first portion to the second portion. In some implementations, the second portion is lower than the first portion while the tray is placed on a flat surface. In some implementations, the first portion is supported by at least one leg while the tray is placed on the flat surface. In some implementations, the first portion comprises at least four sides. In some of those implementations, the first side and the second side of the at least four sides comprise two sidewall portions, the two sidewall portions are connected to the first spout, a third side of the at least four sides is connected to the second portion, and a fourth side of the at least four sides is open to permit access to the first portion for sliding the quantity of pills from the first portion to the second portion.

In some implementations, when the tray is inserted in the imaging device the first portion is disposed outside the imaging device, the second portion is disposed inside the imaging device, and the second portion is positioned in a field of view of a camera in the imaging device.

In certain aspects a method for preparing a prescription for sale is disclosed. The method includes adding a quantity of pills in a prescription to a first portion of a tray, manually counting the quantity of pills to determine a quantity of pills, returning an excess quantity of pills to a storage container through a first spout positioned on a periphery of the first portion. The resultant quantity of pills is slid from the first portion to the second portion. An image is captured of the quantity of pills on the second portion. The quantity of pills is dispensed, responsive to a remote verification of a medication type and the quantity of pills in the image being consistent with the prescription, through a second spout positioned on a periphery of the second portion into a sales container.

In some implementations, the method includes inserting, prior to imaging the quantity of pills, the tray into an imaging device configured to generate the image. The second of the imaging tray portion is lower than the first portion while the tray is placed on a flat surface. The quantity of pills is slid from the first portion to the second portion down a step between the first portion and the second portion.

In some implementations, the method includes capturing the image with a camera at a first site. The method further includes electronically displaying the image on a display at a second site remote from the first site and electronically transmitting a verification from the second site to the first site in response to the image of the quantity of pills being determined at the second site to be consistent with the prescription.

BRIEF DESCRIPTION OF THE DRAWINGS

The present disclosure is illustrated by way of example, and not by way of limitation in the figures of the accompanying drawings in which like reference numerals are used to refer to similar elements.

DETAILED DESCRIPTION

With the advent of artificial intelligence and computer vision, there is an opportunity to virtualize, speed up, and improve the accuracy by which product verification is performed in the pharmacy workflow. An improved verification process in the pharmacy workflow, as described herein, eliminates physical handling of a prescription product by a pharmacist and saves time in the pharmacy workflow. An imaging device may be installed at a site, such as a retail pharmacy, to enable virtual verification. The imaging device captures high quality images of a prescription product, such as pills, tablets, capsules, caplets, liquid bottles, canisters, etc. for a pharmacist (e.g., situated remotely) to virtually verify the prescription product before it is dispensed to a customer at a point of sale. A dispensing application may be installed on one or more pharmacy computing devices in a pharmacy, such as a laptop, tablet, etc., to operate in conjunction with the imaging device to scan, capture, and store data including one or more images of the prescription product.

Figure 1:
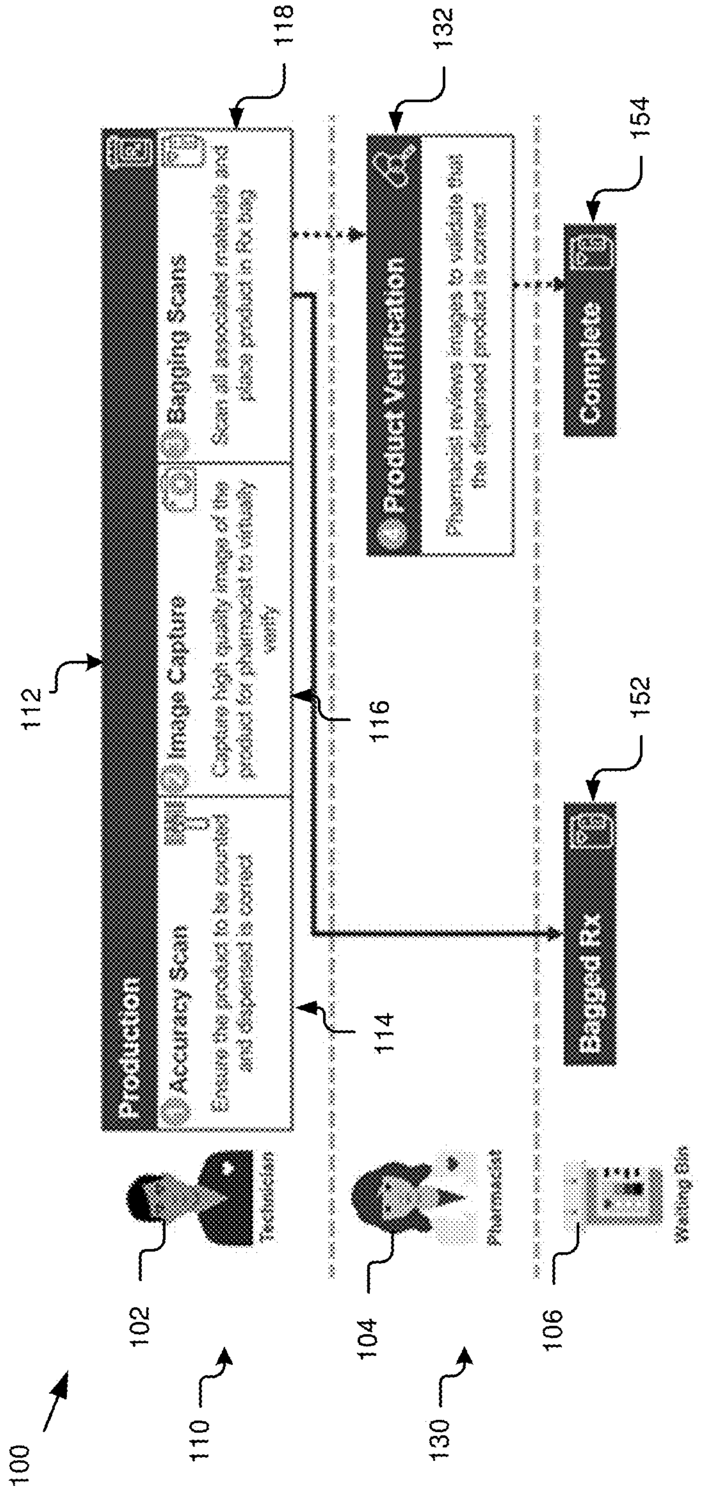
FIG. 1 shows an example workflow for verifying a prescription product during a prescription fill process.

FIG. 1 shows an example workflow 100 for verifying a prescription product during a prescription fill process. A pharmacy or similar workspace may include multiple workstations for processing and fulfilling drug prescriptions wherein one or more workstations perform one or more stages involved in processing prescriptions. Each workstation is designated, and, optionally, is configured, to accomplish one or more tasks. Workstation tasks can be defined in terms of the roles and responsibilities, as well as the skill levels required, of persons who staff each workstation. In addition, definition of workstation tasks can be directed to limiting staff to a single or primary pharmacy customer interface of a workstation to ensure effective customer communication and efficient workflow.

The designated workstations and defined tasks help to create a stage-by-stage process or a compartmentalized workflow whereby each processing stage is handled and/or completed at one or more workstations by one or more staff persons having the requisite skill level, e.g., registered pharmacist (RPh), certified or otherwise trained technician (CT), a customer support associate (CSA) or other support person. In addition, the workstations and tasks are so defined to help to permit early detection and resolution of issues or problems that can occur during processing. Further, the defined workstations and tasks help to distribute the process of prescription fulfillment efficiently among one or more staff persons and help a pharmacy to provide customers with relatively accurate prescription pick-up times that meet customers' needs and expectations.

In part, the system queues and interfaces described herein may guide a technician 102 through the prescription production 112 including 1) scanning 114 the prescription product for accuracy and preparing or filling the prescription order, 2) capturing 116 high quality images of the prescription product, and 3) scanning 118 all materials associated with the prescription product, bagging 152 and placing the prescription product in a waiting bin 106. The registered pharmacist 104 may then be guided through additional system queues and interfaces at their workstation to 4) virtually review the captured images to verify and validate 132 that the dispensed product is correct and complete 154 before it is handed to the customer at the point of sale. Virtual verification of the prescription product, which may be performed at a second site 130, eliminates redundant physical handling of the prescription product by a pharmacist and enables the technician to perform the bulk of the production at a first site 110 including bagging the prescription product for pick up. It should be noted that the first and second sites may be different workspaces collocated within a single pharmacy, or the first and second sites may be physically remote from one another.

Some of the eliminated redundant physical tasks of a pharmacist may include but are not limited to:

1—Retrieving basket,
2—Removing label and product from the basket,
3—Scanning label,
4—Scanning product label,
5—Opening vial,
6—Pouring contents into verification tray,
7—Pouring contents back into the vial,
8—Closing the vial,
9—Retrieve empty prescription bag,
10—Placing contents into the prescription bag,
11—Affixing label to the prescription bag,
12—Stapling the label to the prescription bag, and
13—Placing the prescription bag in the holding area.

Figure 2:
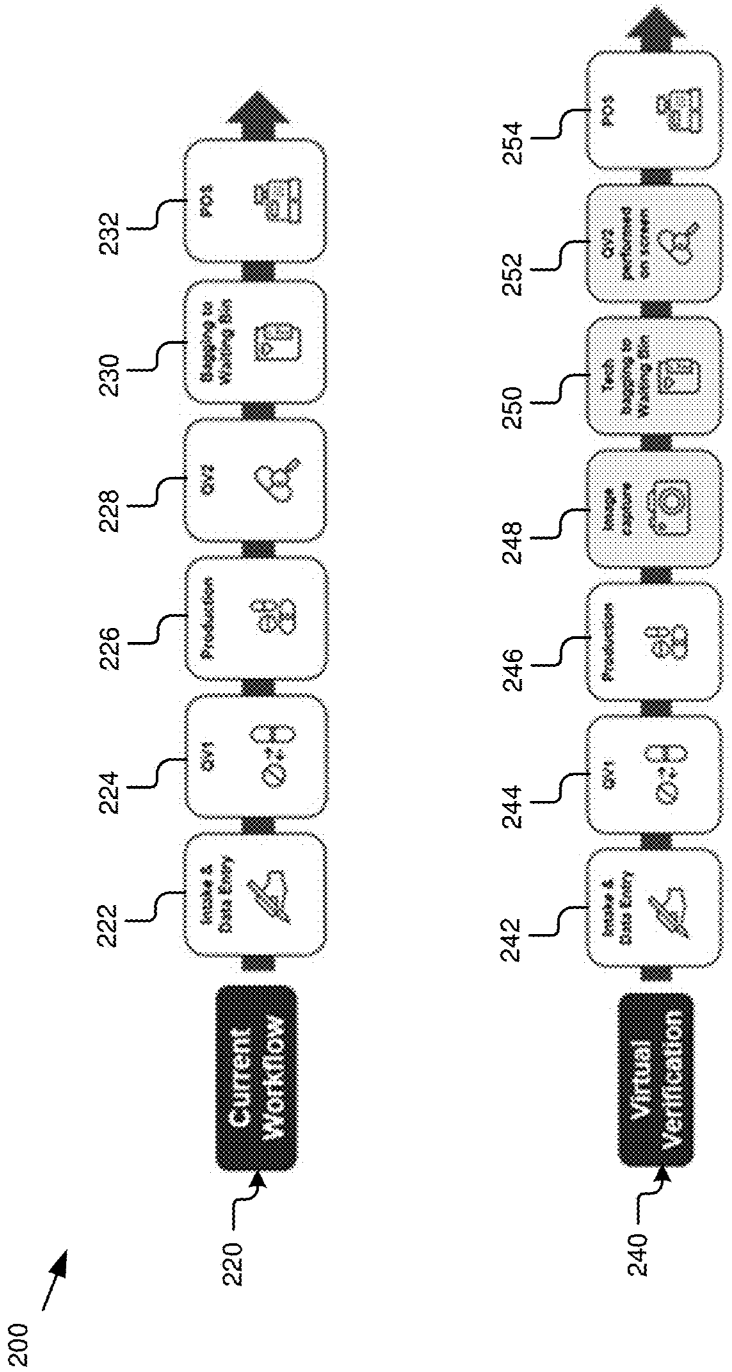
FIG. 2 shows a comparison between a prior pharmacy workflow and a pharmacy workflow including the virtual verification described herein.

FIG. 2 shows a comparison between a current or conventional pharmacy workflow 220, and an improved pharmacy workflow 240 including the virtual verification. For example, in a current or conventional workflow 220, a technician inputs 222 a prescription into a workflow system. In a first quality verification (QV1), the technician verifies in step 224 the bulk prescription product corresponds to the prescription product identified in the prescription. The technician then engages in production 226 by counting and filling the vial according to the prescription. In a second quality verification (QV2), a pharmacist subsequently verifies in step 228 the results of the production by the technician by manually recounting and re-verifying the prescription product in the vial. The pharmacist bags and places 230 the filled prescription product in a waiting bin in preparation for a patient to purchase 232 the prescription product at a point-of-sale location. As noted, the prescription product is handled in step 224 and re-handled in step 228. A re-handling of the product injects delay and subjects the prescription product to compromise and errors in the workflow process.

For example, one implementation of the improved pharmacy workflow 240 shown in FIG. 2, eliminates the second or subsequent re-handling of the prescription product. The technician as part of his or her workflow fills the prescription as per order (production), places the prescription product in an imaging device, captures one or more images of the prescription product, scans a barcode on the prescription product, bags and places the prescription product in a waiting bin. In a second implementation of the improved pharmacy workflow 240, the technician then scans product for accuracy at dispensing system, places the product on imaging device, captures pictures, labels, and scans product labels, places the prescription into a bag, and transfers to waiting bin/will-call area.

Specifically, a technician inputs 242 a prescription into a workflow system. In a first quality verification (QV1), the technician verifies in step 244 the bulk prescription product corresponds to the prescription product identified in the prescription. The technician then engages in production in step 246 by counting the prescription product according to the prescription. A camera at a first site, the technician site, captures in step 248 an image of the prescription product to be dispensed according to the prescription of the patient. The technician then packages in step 250 the prescription product for sale at the site of the technician prior to receiving a verification from a pharmacist. The packaged prescription product may then be sealed and placed in a waiting bin by the technician. A second quality verification (QV2) 252 is then performed by a pharmacist in response to the system electronically displaying an image on a display of the prescription product to be dispensed according to the prescription to the patient.

The pharmacist as part of his or her workflow then initiates review via the queue-based system, verifies the prescription product on screen using the captured images (QV2), and approves the bagged prescription for customer pick-up if the product is deemed to have been dispensed accurately. The pharmacist may electronically transmit a verification from a location of the pharmacist to a location of the technician and the filled prescription in response to the image of the prescription product being determined at the location of the pharmacist, such as a second site, to be consistent with the prescription. The verified prescription product may then be eligible for purchase 254 by the patient at point-of-sale. If the pharmacist is unable to verify the prescription product via the image (e.g., the picture is blurry, or an image is missing) the pharmacist may opt to systematically send the prescription back to the technician to be re-imaged, or to retrieve the bagged prescription from the waiting bin area to physically inspect the dispensed product themselves.

As noted, steps 242, 244, 246, 248, 250, and 254 may be performed by a technician at a first site, and step 252 may be performed by a pharmacist referencing an image of the prescription product at a second site or separate workstation. Such an aspect allows the technician and the pharmacist to be physically remotely located from one another and eliminates a subsequent handling of the physical prescription product by, for example, the pharmacist.

Figure 3:
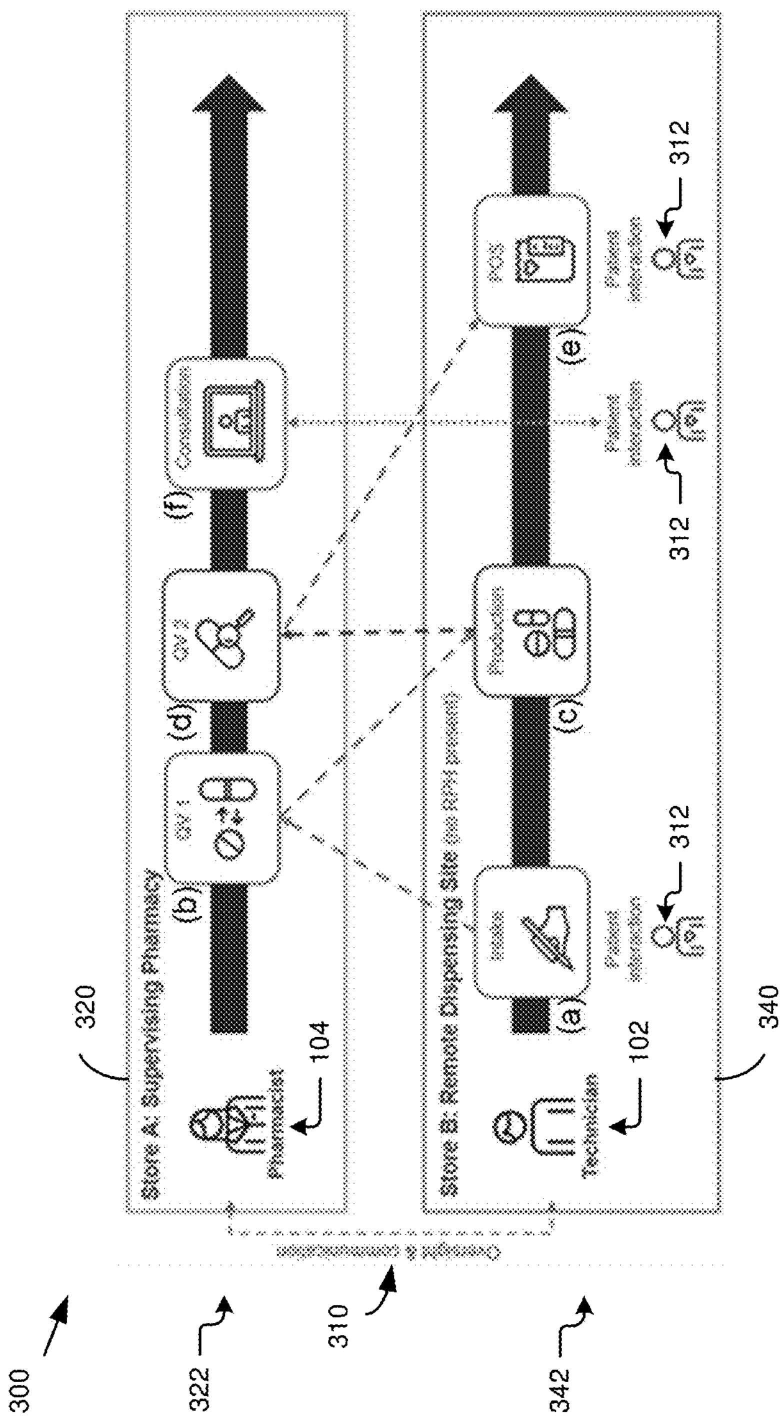
FIG. 3 shows an example of a bifurcated workflow between a supervising pharmacy and a remote dispensing site for verifying a prescription product during a prescription fill process.

FIG. 3 shows an example of a bifurcated workflow between a supervising pharmacy 320 and a remote dispensing site 340 for verifying a prescription product during a prescription fill process 300. A telepharmacy or a remote dispensing site (e.g., Store B) 340 may include a technician 102 and operate without a registered pharmacist physically present at that location. The technician 102 at the telepharmacy or remote dispensing site 340 may coordinate with a supervising pharmacy (e.g., Store A) 320 which includes a registered pharmacist 104. The registered pharmacist 104 at the supervising pharmacy 320 may act as a consultant and oversee the operation of the telepharmacy via a communication link 310. The pharmacy workflow process 300 may be bifurcated into a technician workflow 342 at the remote dispensing site 340 and a pharmacist workflow 322 at the supervising pharmacy 320.

For instance, as shown in FIG. 3, the technician workflow 342 may include step (a) interacting with the patient 312 and performing intake by entering the prescription into a pharmacy computing system, step (c) preparing the prescription fill in production and capturing high quality images of the prescription product for the pharmacist 104 to review, and step (e) completing the transaction with the patient 312 at the point of sale after the pharmacist 104 has virtually verified and approved the prescription fill. The pharmacist workflow 322 may include step (b) virtually overseeing the prescription entry by the technician 102 at intake, step (d) virtually verifying and approving the prescription fill by the technician 102, and step (f) consulting virtually with the patient 312 to resolve any issues or address patient's needs.

Figure 4:
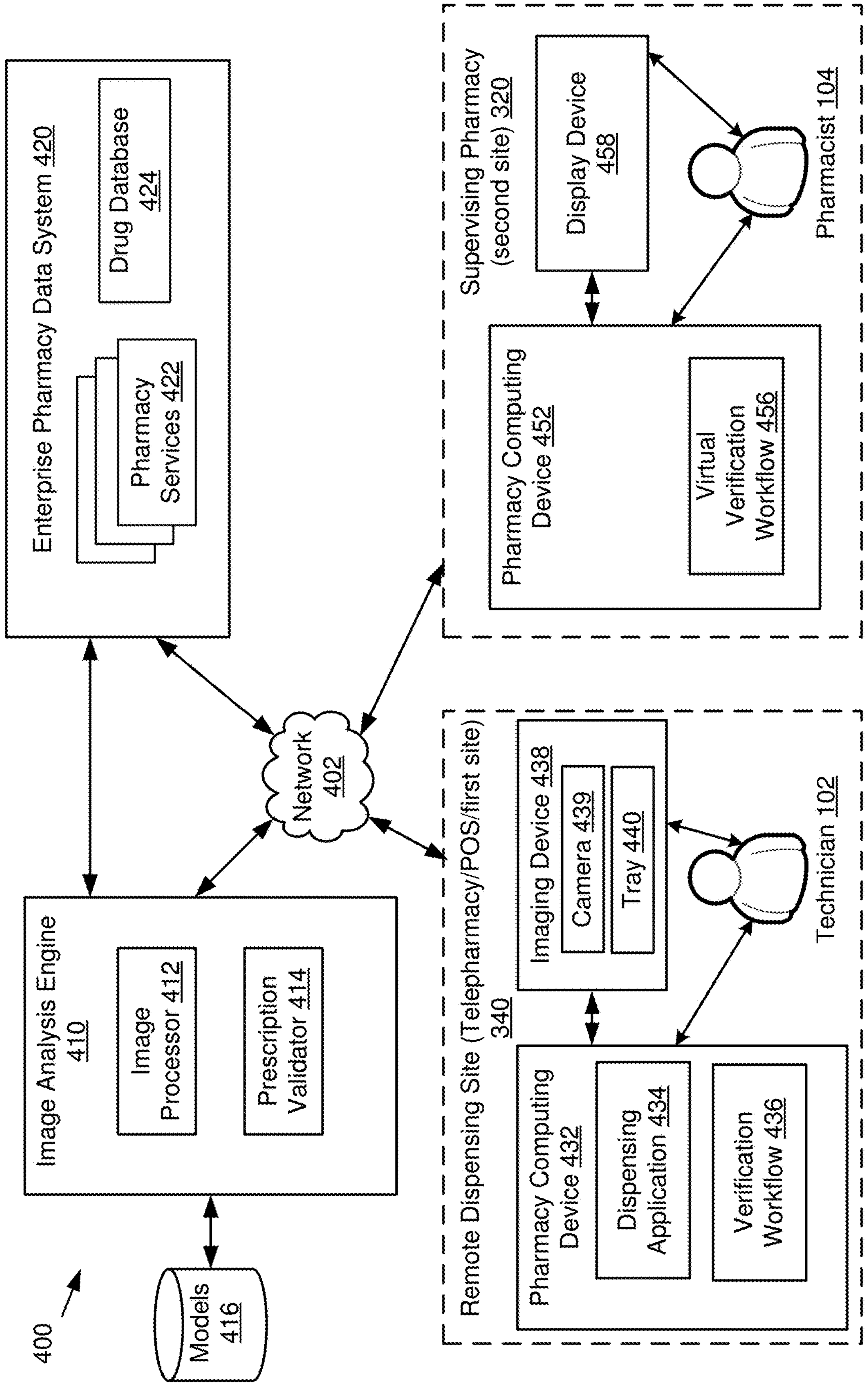
FIG. 4 shows an example implementation of system for image analysis and virtual verification of prescription product used in a pharmacy workflow.

FIG. 4 shows an example implementation of system 400 for image analysis and virtual verification of prescription product used in a pharmacy workflow. As shown in FIG. 4, retail pharmacy system including remote dispensing site 340 and a supervising pharmacy 320, and an enterprise pharmacy data system 420 may be configured to interact with an image analysis engine 410 to enable virtual verification of prescription product in a pharmacy workflow. As noted previously, the remote dispensing site 340 and supervising pharmacy 320 may be at separate physical sites or may be co-located within the same physical site but physically separated (e.g., at different workstations, in different buildings, in different rooms, etc.). The image analysis engine 410 may be embodied in a combination of software modules supporting the pharmacy dispensing application 434 and verification workflow 436 at the remote dispensing site, locally on the pharmacy computing device and/or served over a network from the enterprise pharmacy data system. For example, some data and functions may be stored in local data on the pharmacy computing device, while other data and functions may be accessed through an API in the enterprise pharmacy data system.

In some implementations, a pharmacy system may include a pharmacy computing device 432 and an imaging device 438 including a camera 439. The pharmacy computing device 432/452 used by the pharmacist and/or technician may similarly use a combination of local computing resources and network computing resources 402 for coupling with the enterprise pharmacy data system 420. An imaging device 438 may be configured to be coupled to the pharmacy computing device 432 for capturing high quality images of the prescription product. In some implementations, the captured data from the camera 439 of the imaging device 438 may be loaded and adjusted (e.g., white balance, noise reduction, etc.) using the pharmacy computing device 432 and subsequently sent to the image analysis engine 410 for analysis.

The pharmacy dispensing application 434 may control or receive data from the enterprise pharmacy data system 420 and image analysis engine 410, identify and format the relevant data for presentation to the pharmacist 104 and/or technician 102. In some implementations, the verification workflow 436 may be part of the prescription fulfillment workflow in a pharmacy system 400. In some implementations, the information for presentation to the pharmacy staff may be displayed on a visual interface 458 of the pharmacy computing device 432. There may be multiple pharmacy systems 320/340 configured to interact with each other and the enterprise pharmacy data system 420. For example, it may be that some retail pharmacies act as supervising pharmacies 320 and house a pharmacist 104 to oversee and verify the prescription workflow of a technician 102 in a telepharmacy or other remote location.

In some implementations, the enterprise pharmacy data system 420 may host a number of pharmacy services 422 and a drug database 424. For example, pharmacy services 422 may include prescription reorder, prescription delivery, linkage to specific savings programs, subscription fill services, bundling additional prescriptions for refill/pickup, automating next refill, conversion to 90-day prescriptions, clinic services, flu shots, vaccines, non-prescription products, etc. The drug database 424 may include information about prescription and over-the-counter medication. In particular, the drug database 424 may include proprietary or in-house databases maintained by pharmacies or drug manufacturers, commercially available databases, and/or databases operated by a government agency. The drug database 424 may be accessed using industry standard drug identifiers, such as without limitation, a generic product identifier (GPI), generic sequence number (GSN), national drug code directory (NDC), universal product code (UPC), health related item, or manufacturer.

The imaging device 438 via camera 439 may support imaging prescription products of all types. In some implementations, the imaging device 438 uses a Counting and Imaging Tray (CAIT) 440 as shown in detail in FIG. 5.

Figure 5:
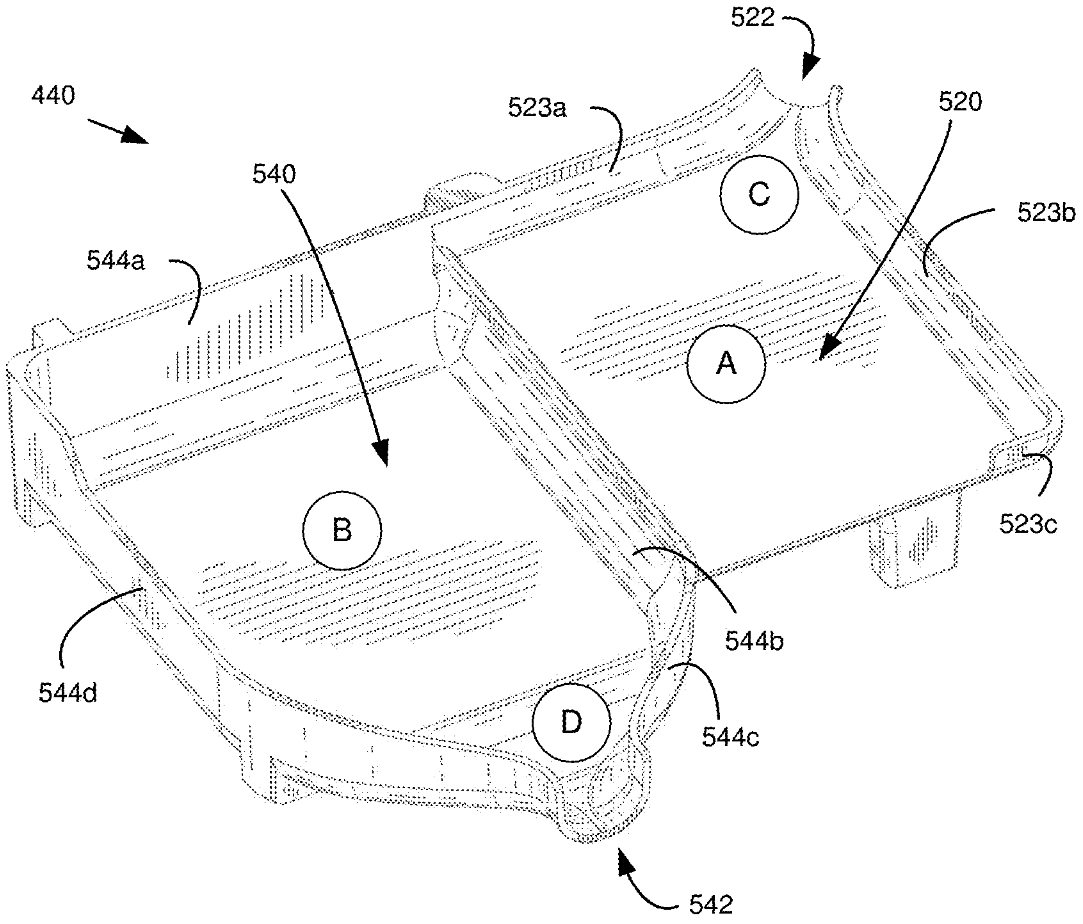
FIG. 5 shows an example implementation of a counting and imaging tray in accordance with the present disclosure.

In FIG. 5, the CAIT 440 may be used by a pharmacy staff member, such as technician 102, to both count and take an image of the prescription, such as pills without needing to dump the pills from the tray into another container or tray for capturing images. As shown in FIG. 5, the pharmacy staff member may:

1—Pour pills from a stock bottle of the prescription product onto a first portion or a counting level (A) 520 during a prescription workflow;

2—Count and swipe the prescribed quantity of pills onto a second portion of imaging level (B) 540;

3—Pour the remaining amount on the counting level (A) back into the stock bottle via a spout or chute (C) 522 at one of the corners of the counting level (A) 520;

4—Slide the CAIT 440 into the imaging device 438 to capture one or more images of the prescribed quantity; and 5—Pour the contents into a vial or bottle via another spout or chute (D) 542 at one of the corners of the imaging level (B) 540.

As shown in FIG. 5, the CAIT 440 is particularly advantageous because of the different spouts or chutes (C) 522 and (D) 542 for inputting and dispensing the prescription, the different layers at different heights for counting and imaging, and the walls around each layer of the CAIT that are sloped or angled to bias or direct the pills towards the next area of processing from input spout or chute (C) to output spout or chute (D). The first portion or counting level (A) includes a top surface onto which the pills are poured from the stock bottle. The walls 523*a*, 523*b*, and 523*c* partially enclose the first portion. The wall 523*a* which is furthest from the pharmacy tech spans the full length of the first portion. In the example shown, wall 523*a* merges into the wall 544*a* of the second portion. Wall 523*a* also forms one side of spout or chute 522. Wall 523*b* is perpendicular to wall 523*a*. Together wall 523*a* and wall 523*b* form the sides of the spout 522. In some embodiments, such as that depicted here, wall 523*c* does not span a full side of the first portion, instead wall 523*c* is abbreviated, and the majority of the side of the first portion facing the pharmacy tech is open.

The second portion or imaging level (B) 540 is positioned so that when the CAIT is placed on a flat surface, such as a countertop or table, the second portion or imaging level 540 is lower than the first portion. The difference in height creates a physical barrier for moving the pills from the second portion to the first portion. The pills moved to the second portion would be unable to slid back to the first portion because of the step created by the lower position of the second portion with respect to the height of the first portion. In the example shown, at least one leg 524 supports counting level (A), along with the side wall 544*b* of imaging level (B) that is adjacent to counting level (A).

The second or imaging portion of the CAIT is configured to assist in imaging the pills. The CAIT further includes an outlet spout (D) 542. In the example shown, spout (D) 542 is formed in wall 544*c*, which curves out from side walls 544*b*, 544*d*, and imaging area (B). In one aspect, the CAIT is further configured with at least one slope within the second portion of the tray (e.g., imaging level (B) 540) to bias the pills toward the field of view of the camera 439 in the imaging device 438.

Figure 6:
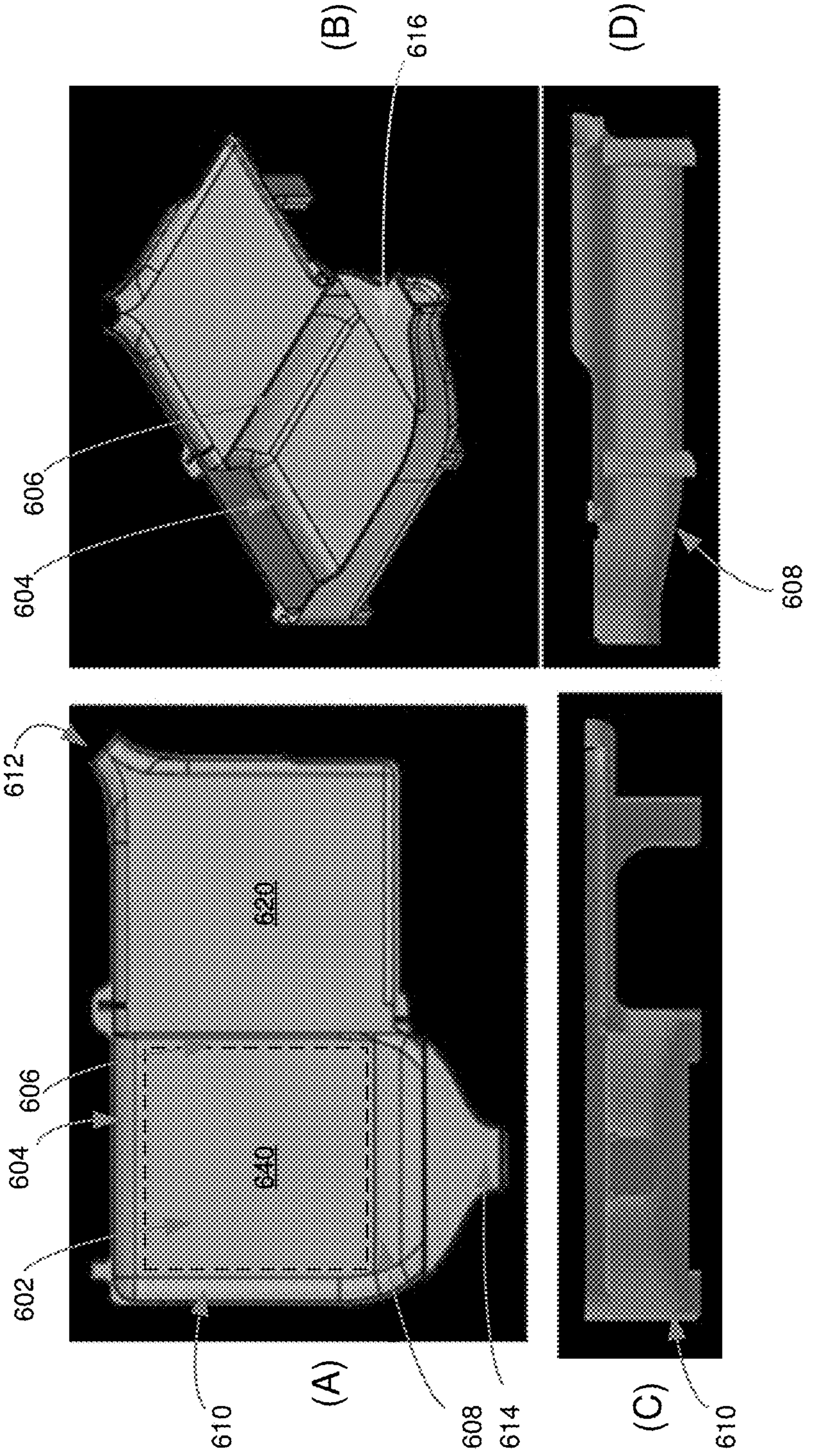
FIG. 6 shows a top view, a perspective view, a front view, and a left side view of the example implementation of a counting and imaging tray.

FIG. 6 illustrates different views of the CAIT used in conjunction with an imaging device. The CAIT 440 is illustrated with respect to various views (A)-(D). View A is a top-down view of the CAIT 440. The CAIT 440 is illustrated as including a counting or first portion 620 and an imaging or second portion 640. The counting or first portion 620 is similar to the first portion/counting level (A) 520 in FIG. 5 and the imaging or second portion is similar to the second portion/imaging level (B) 540 in FIG. 5. The imaging portion 640 is illustrated as including a field of view area 602 which is formed in response to various sloped contours 604, 606, 608, and 610 within the imaging portion 640 that bias or direct prescription product into the field of view area 602. As in FIG. 5, CAIT 440 includes two spouts or chutes, a first chute 612 in communication with the first/counting portion 620 and a second chute 614 in communication with the second/imaging portion 640.

View B is a perspective view. This view illustrates the difference in height between the first portion 620 and the second portion 640. The first portion 620 is positioned higher than the second portion 640 when the CAIT is placed on a flat surface. Further, the CAIT 440 is illustrated to include top cap 616 enclosing spout 614 to assist in retaining the prescription product in the imaging portion 640 when the product is poured from the CAIT 440 into a vial (e.g., pill bottle). The sloped contour 608 slopes upward from the base of the second portion to the second spout or chute.

Figure 7:
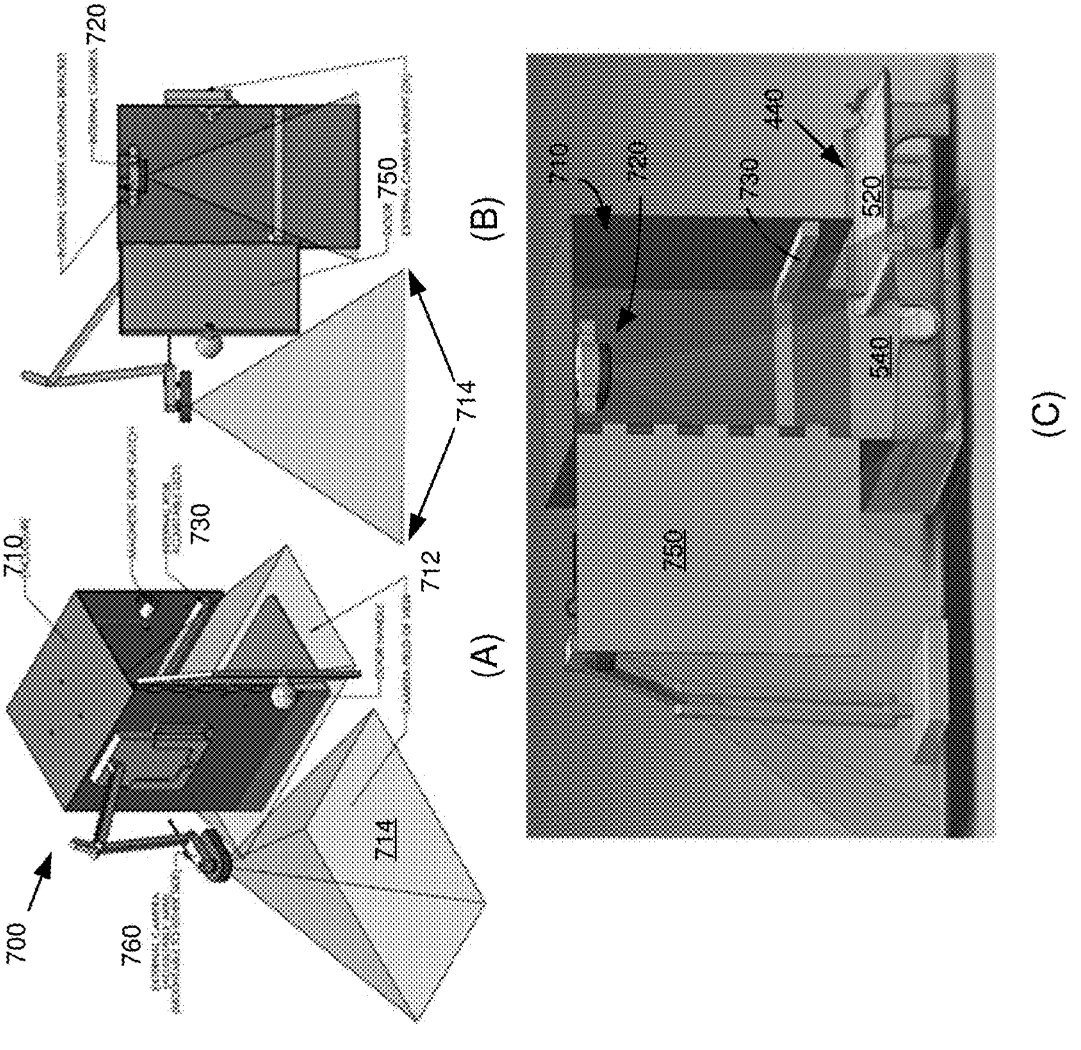
FIG. 7 shows an example imaging device with a dual camera configuration in accordance with the present disclosure.

FIG. 7 illustrates an example imaging device 700. In one aspect, a single camera 720 configuration is illustrated for capturing high quality images of the prescription product using a CAIT 440. In another aspect, a dual camera (e.g., first camera 720 and second camera 760) configuration is illustrated for capturing high quality images of the prescription product using a CAIT 440. In FIG. 7, various views (A)-(C) are presented. In view (A), a perspective view of the imaging device 700 is illustrated. In view (B), a frontal cross-sectional view is illustrated. In view (C), a configured view is illustrated that shows the CAIT 440 inserted into the imaging device 700.

The imaging device 700 includes a self-standing enclosure 710 for housing and supporting various structures, including a first camera 720. The first camera 720 is configured to attach above a working surface to provide a field of view 712 over the working surface. Further, the field of view corresponds to the imaging level 540 of CAIT 440. The camera 720 is illustrated as being attached to the top inner surface of enclosure 710. The camera 720 is attached to the enclosure using an internal camera mounting bracket, such that the field of view creates a consistent depth of field for imaging portion 540.

The enclosure 710 further includes a door 750 configured to provide access to the imaging level 540 of CAIT 440 when the CAIT 440 is inserted into the imaging device 700. The CAIT is inserted into the enclosure of the imaging device through an opening in one side of the enclosure. The opening is sized so that the CAIT will slide into the enclosure. The door is attached to the enclosure so that the hinge of the door is opposite the opening for the CAIT. The door includes a doorknob adjacent the side of the door opposite the hinges. The door is secured in a closed position by a magnetic door catch.

In operation, the CAIT is inserted into the imaging device 700 and the door 750 is closed. The interior of the imaging device in the field of view 712 is protected from intermittent exterior lighting variations. Accordingly, to provide improved lighting conditions for the first camera 720 to capture images of prescription product in the imaging level 540 of the CAIT 440, the imaging device 700 may further include one or more lights 730. In one example, the lights 730 are configured to illuminate the second portion or the imaging level 540 of the CAIT 440. For example, the lights 730 may be a row of adjustable light emitting diode (LED) lights surrounding multiple sides of the inside of enclosure 710.

The imaging device 700 may include a second camera 760 coupled to an exterior surface of enclosure 710. The second camera 760 may be coupled to the exterior surface of the enclosure by a support arm. The support arm is a swivel arm camera mount movable to multiple positions. The second camera 760 may be utilized when imaging prescription product needing a field of view 714 greater than the field of view 712 within the enclosure. For example, if a tray including prescription product is too large to be received within the enclosure 710, then the external second camera 760 may be utilized. In other implementations, the second camera 760 may also be used for additional capacity by the imaging device 700.

With respect to FIG. 7, in one use case, the pharmacy staff member may slide the CAIT 440 containing prescription production (e.g., loose pills) on the imaging level 540 into the imaging device 700 and capture images of the imaging level 540 using an internal high definition (HD) camera 720 inside the imaging device. In another use case, the pharmacy staff member may open the imaging device to place boxes and stock bottles inside the imaging device 700 to capture one or more images without using the CAIT 440. In yet another use case, the pharmacy staff member may switch to an external camera 760 affixed to the imaging device 700 or a stand-alone camera coupled to the imaging device 700 to capture images of prescription products that do not fit inside the imaging device.

Figure 8:
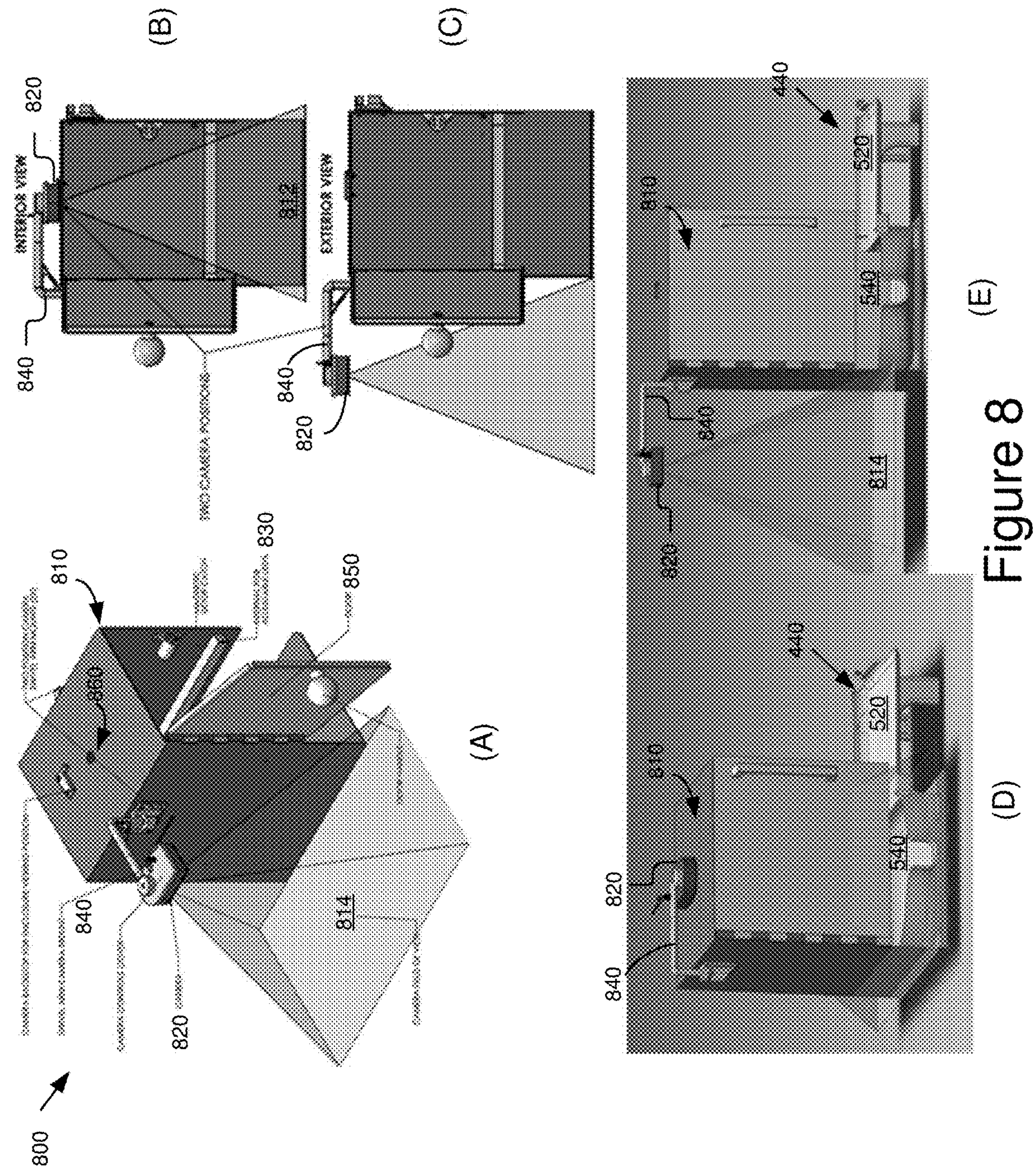
FIG. 8 shows an example imaging device with a single camera configuration in accordance with the present disclosure.

FIG. 8 illustrates an example imaging device 800 using a single camera 820 configuration for capturing high quality images of the prescription product using a CAIT 440. In FIG. 8, various views (A)-(E) are illustrated to show the imaging device 800 from various perspectives and in various states of use. The imaging device 800 includes an enclosure 810 and may include a door 850 and lights 830 corresponding to the elements described with respect to FIG. 7. The implementation illustrated in FIG. 8, utilizes a single camera 820 for capturing images within the enclosure (see views (B) and (D)), and for capturing images outside of the enclosure (See views (A), (C), and (E)). To accommodate capturing images in both positions using a single camera 820, the imaging device 800 includes a swiveling support arm 840 maneuverable between a first position placing the camera 820 over an aperture 860 to facilitate capturing images of prescription product within a field of view 812 inside of the enclosure 810, and a second position placing the camera 820 extending from the enclosure 810 to facilitate capturing images of prescription product within a field of view 814 outside of the enclosure 810. The swiveling support arm 840 may couple to a portion of the enclosure 810 to provide adequate displacement between the first and second positions. In some embodiments, the support arm 840 is restricted in its positioning to two positions, a first position which images objects within the enclosure, and a second position which images objects outside the enclosure. In these embodiments, the support arm is restricted to movement between these two positions by at least a camera backstop extending from the top surface of the housing for the enclosure viewing position.

In some implementations as illustrated with respect to FIG. 4, FIG. 7 and FIG. 8, the camera (internal and external) coupled to the imaging device may provide a livestream of the image preview to the display of a pharmacy computing device 432 to aid the technician (e.g., staff member) in using the CAIT 440 with the imaging device 700/800. In some implementations, the imaging device transmits the images captured and/or camera livestream to the pharmacy computing device for processing (e.g., white balancing) and image analysis (e.g., prescription count). In some implementations, the imaging device transmits the images captured and/or camera livestream to the image analysis engine 410 for processing and image analysis.

In some implementations, the image analysis engine 410 may include an image processor 412 and a prescription validator 414. The image processor 412 works in conjunction with the dispensing application 434 at the pharmacy computing device 432 to capture, store, retrieve, and delete images of prescription product. In some implementations, the dispensing application 434 sends the captured images from the imaging device to the image processor 412. The image processor 412 receives the image and processes the image. For example, the image processor 412 corrects white balance in the image. The image processor 412 creates an image identifier to associate with the image. The image processor 412 stores the image and the corresponding image identifier in a data storage associated with the image analysis engine.

In some implementations, the image processor 412 receives a request to delete one or more images of a prescription product from the dispensing application 434. The image processor 412 identifies one or more images of the product using an associated image identifier and accordingly deletes the images in the data storage. In some implementations, the image processor 412 may retrieve an image of the prescription product from the data storage and send it to the dispensing application 434 in response to receiving an image identifier corresponding to the image. For example, a pharmacist may retrieve images of prescription products to verify the prescription fill during a verification workflow on the pharmacy computing device.

Figure 9A:
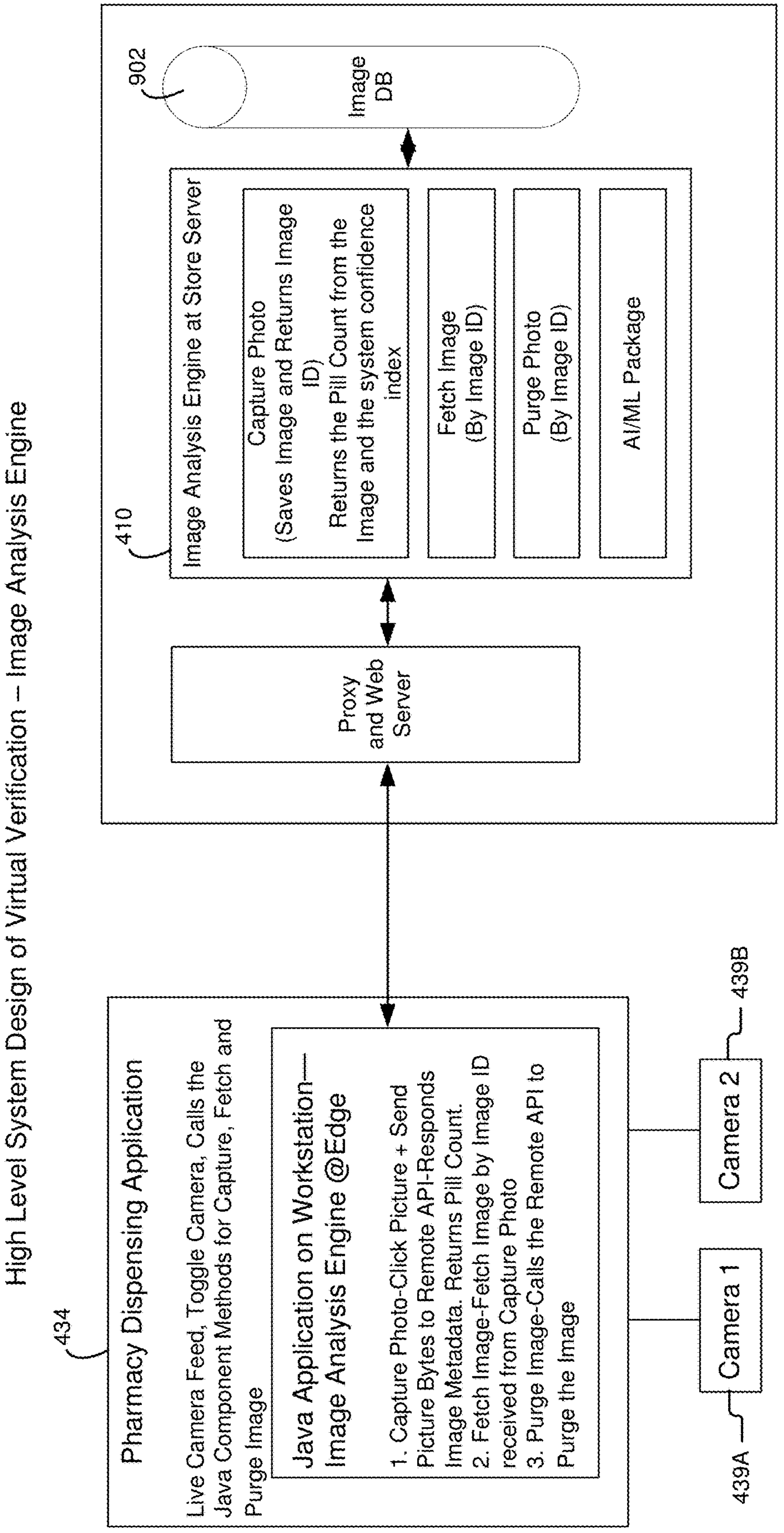
FIG. 9A shows an example high level architecture diagram depicting an interaction between a dispensing application and an Image Analysis Engine for implementing virtual verification.

FIG. 9A shows an example high level architecture diagram depicting an interaction between a dispensing application 434 and an Image Analysis Engine 410 for implementing virtual verification. In some implementations, the prescription validator analyzes the image from the image database 902 captured by camera 439 for determining a count of prescribed pills and flags the image if the count does not match the prescription. In one example, the pharmacy dispensing application 434 may support a live camera feed, toggle between cameras 439A and 439B, and call the Java components for capture, fetch, and purge image(s). In one example, the image analysis engine 410 may capture the image, save the image, return an image ID, and return a pill count from the image and also return a system confidence index.

Figure 9B:
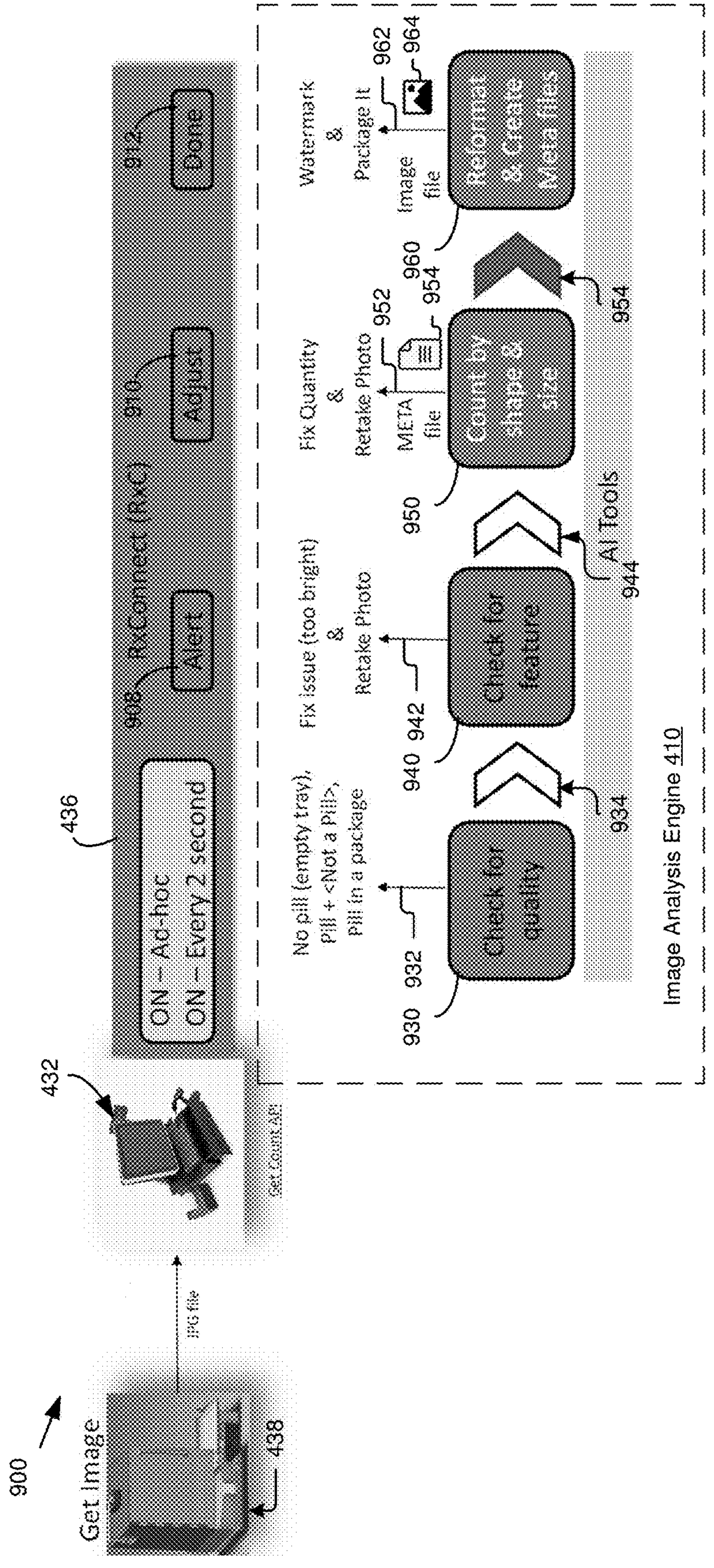
FIG. 9B shows an example of processing of an image for virtual verification at a remote site.

FIG. 9B shows an example flow diagram for processing an image. In some implementations, a process 900 generated image at imaging device 438. In some implementations, a pharmacy computing device 432 may couple to an imaging device 438. In some examples, the imaging device 438 may be configured to capture an image of prescription product and transfer that image, for example in a JPEG file, to the pharmacy computing device 432. The pharmacy computing device 432 may initiate, for example, an API call to the image analysis engine 410. Image analysis engine 410 may include or access various artificial intelligence (AI) tools that operate in conjunction with various models 416 of FIG. 4.

The various AI tools may include a data classifier 930 configured to look for a quality of the image, for example, attempts to identify shapes that may be consistent with the shapes of the prescription product (e.g., pills). In some examples, when the data classifier 930 fails to identify shapes consistent with the prescription product, an exception 932 is generated which may create an alert 908 and a verification workflow 436. The alert 908 may also generate an adjustment request 910 which specifies a manual adjustment or removal of items from a CAIT 440 or the field of view of the camera in the imaging device 438.

In response to the data classifier 930 determining that the image includes shapes consistent with the prescription product, the data classifier 930 advances processing 934 to a data classifier 940. The data classifier 940 is configured to look for features of the image, for example, to determine the brightness of the image. In some examples, when the data classifier 940 determines that the features in the image are, for example, too bright or too dim, the data classifier 940 generates an exception 942 which may generate an alert 908 and the request for adjustment 910 to retake the photo.

In response to the data classifier 940 determining that the image includes identifiable features, the data classifier 940 advances processing 944 to a data classifier 950. The data classifier 950 is configured to count individual features in the photo to generate a specific count of the quantity of prescription product. In response to the data classifier 950 determining that the quantity may not be calculated, for example, based upon ones of the prescription product being stacked, or otherwise only partially visible, the data classifier 950 generates an exception 952 designating the quantity as being unresolvable. The data classifier 950 may also generate a metafile 954 designating a partial count of the prescription product. The exception 952 may also generate a manual adjustment request 910 instructing a user to manually adjust (e.g., unstack pills) prescription product in the field of view of the camera of the imaging device 438.

In response to the data classifier 950 resolving or generating a count of the prescription product, the data classifier 950 advances processing metafile 954 to data classifier 960. In some examples, the data classifier 960 reformats the image by placing a watermark on the image for use and tamper identification. The data classifier 960 also creates a metadata (e.g., meta file) that may include a quantity count and other identifiable information relevant to the prescription product. The metadata and modified image may be output 962. The output 962 may also instruct the verification workflow 436 to package (e.g., fill the vile) with the prescription product. Once the prescription product is packaged, the technician can designate the workflow as being complete by asserting a done signal 912.

It should be noted that while multiple models have been illustrated, a lesser or greater number of models may be employed by adjusting the sophistication of each of the models. Further, the image analysis engine 410 may employ machine learning that utilizes deep learning, employs models that may detect only certain types of pills, or may include models that are trained for various characteristics including shape, size, color, and embossments on the prescription product.

Figure 10:
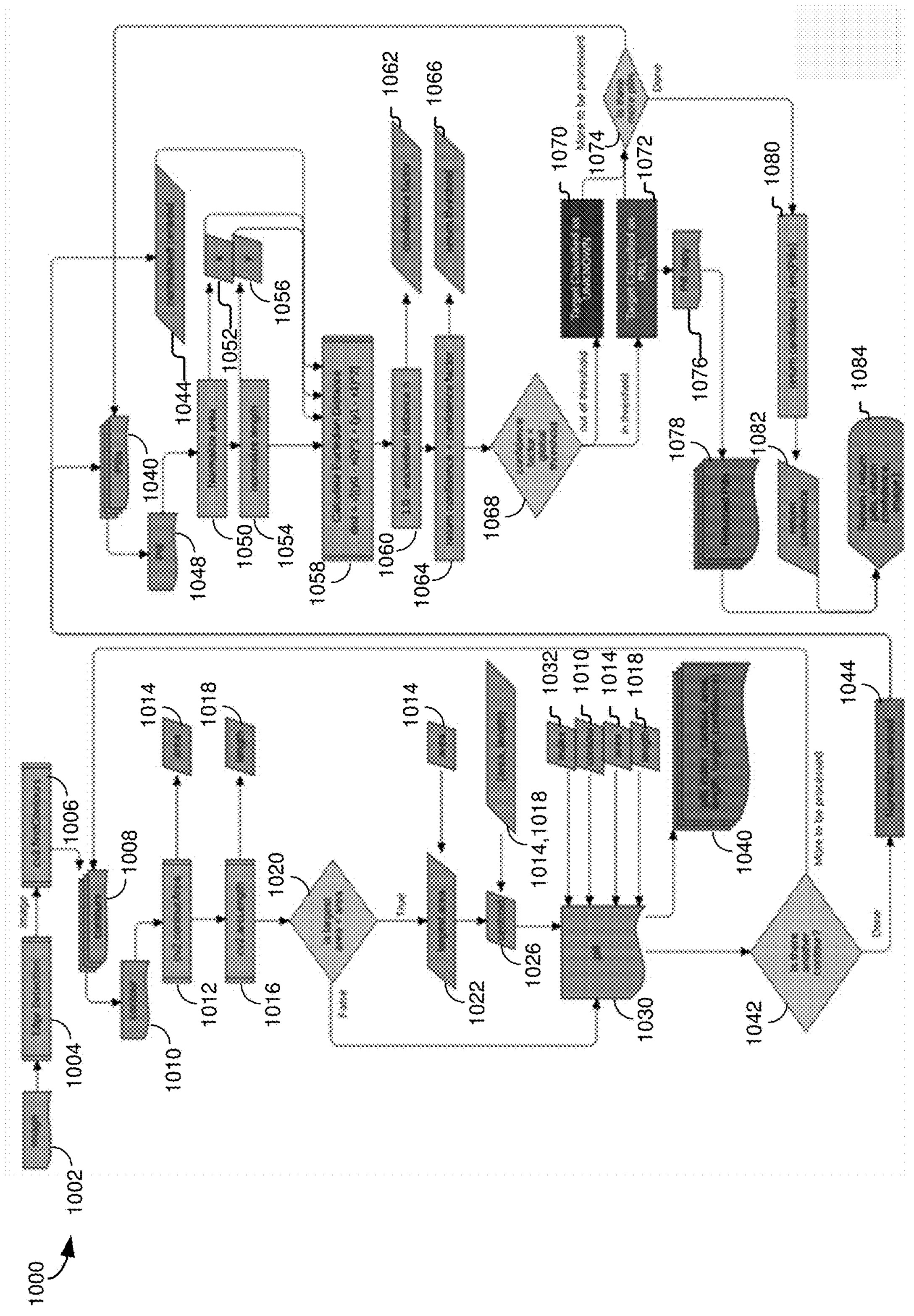
FIG. 10 is a flowchart showing one implementation for a process implemented by the prescription validator for counting an amount of the prescription product in an image and returning a confidence interval associated with a count.

FIG. 10 describes a process implemented by the prescription validator 414 for counting an amount of the prescription product in an image and returning a confidence interval associated with any mismatch in the count. In some implementations, the prescription validator analyzes the image using artificial intelligence (e.g., one or more machine learning models) to identify a type of prescription pill in the image. For example, the prescription validator may analyze the image to detect any anomaly (e.g., presence of an ibuprofen pill mixed in with pills for treating blood pressure) in the total count of pills in the image. The machine learning models may be previously trained using an appropriate data set of images to predict a label for a particular type of pill in an image. Examples of machine learning models may include but are not limited to k-nearest neighbors, convolutional neural network, support vector machines, decision trees, Bayesian networks, random decision forests, linear regression, least squares, other machine learning techniques, and/or combinations of machine learning techniques.

In one implementation, an image 1002 is captured as previously described, and a process 1004 performs edge detection on the image. The edges are used in a process 1006 to identify contours. The contours are stored as contours 1008 with a current one being processed as contour 1010. A process 1012 determines an area 1014 of the current contour 1010. Process 1016 determines an arc length 1018 for the current contour 1010. The comparison 1020 compares the area 1014 with a previously stored area. When the area 1014 is greater than the previously stored area then the area 1014 is stored as the largest area 1022. In a process 1026, a centroid is determined from the previously determined area 1014 and length 1018. A process 1030 determines from inputs of index 1032, contour 1010, area 1014, and length 1018 if the combination of the inputs is consistent with the identification of the pill. Accordingly, the result of pills 1040 is stored as a pill with an index, contour, area, length, target, and confidence level. A query process 1042 determines if there is another contour, meaning more contours to be processed. When more contours are determined, processing returns to processing the next contour.

When query 1042 determines that there are no other contours to be processed, a process 1044 normalizes the centroid. The pills 1040 are then analyzed one pill at a time starting with a pill 1048. Process 1050 normalizes the area and generates a normalized area 1052. A process 1054 normalizes the length and generates an output 1056. Process 1058 determines a distance based upon the normalized area, the normalized length, and the normalized centroid. A process 1060 determines a confidence factor 1062.

A process 1064 determines a return threshold 1066. The threshold is used in query to gauge a confidence factor that a determined pill was likely detected. A query 1068 determines whether the confidence factor is less than the global threshold. If the confidence factor is out of the threshold, then the target area is classified as unknown 1070. If the confidence factor is within the threshold, then the target area is classified as a pill 1072. Further, if the confidence factor is within the threshold, a pill copy 1076 is generated and stored as returned pills 1078. A pill copy 1076 is an image that was classified to be a pill based on the above process.

When a query process 1074 determines there are more pills for processing, then processing returns to process the next pill 1040. When the query process 1074 determines there are no more pills for processing, then a process 1080 returns a confidence per pill resulting in the generation of a return confidence 1082. Process then generates an output 1084 based upon the pill count, the confidence, and the image. Specifically, the pill count, confidence factor/level, and image are illustrated below with respect to the outputs illustrated in FIG. 12C.

Figure 11:
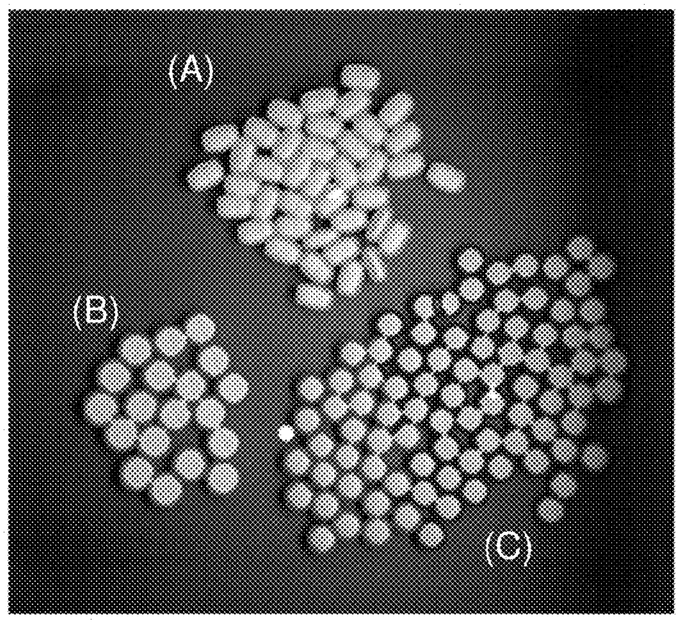
FIG. 11 shows a graphical representation of an example output obtained from analyzing an image of pills using K-nearest neighbors or K-means clustering.

FIG. 11 shows a graphic representation of an example output obtained from analyzing an image of pills using K-nearest neighbors or K-means clustering. Illustrated is an example of K-nearest neighbor supervised machine learning training for pill classification. In some implementations, image segmentation or templating can be used to cluster groups (A), (B), and (C) of detected pills or find anomalies. This is the process of slicing the image into several layers, then iterating a kernel across each slice.

Figure 12A:
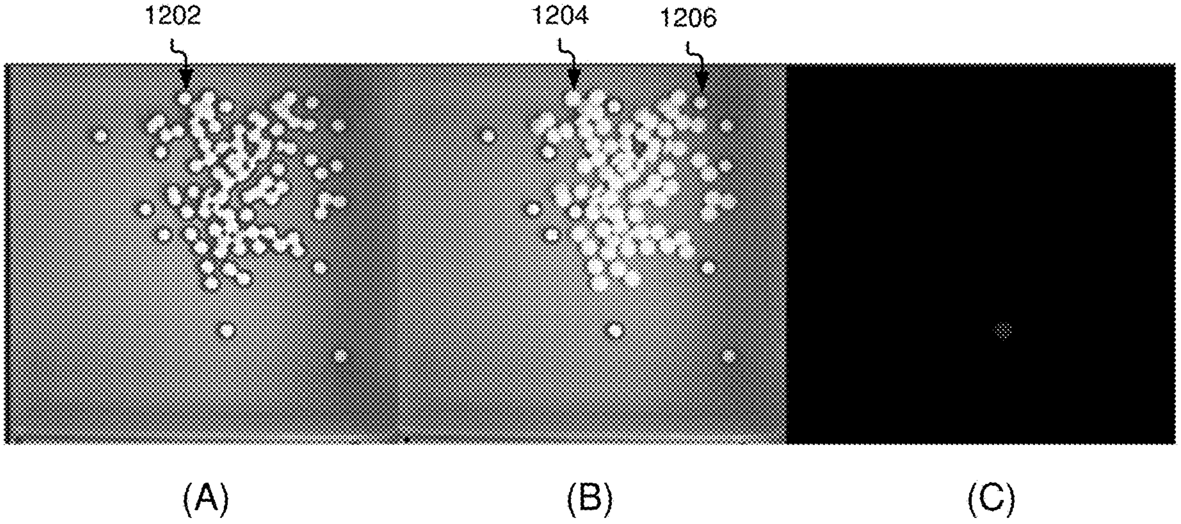
FIG. 12A shows a graphical representation of an example output obtained from analyzing an image of pills using image segmentation or templating.

FIG. 12A shows an example output obtained from analyzing an image of pills using the process described with respect to FIG. 10. Illustrated is an artificial intelligence (AI) segmentation/slicing of images to identify anomalies or comingling of pills. Specifically, view (A) illustrates an input image, view (B) illustrates an intermediary step, and view (C) illustrates an output of the process with an anomaly detected. In some implementations and with reference to FIG. 4, the prescription validator 414 may be instantiated within the dispensing application 434 on the pharmacy computing device 432 and configured to receive a livestream feed from the imaging device 438 and analyze the images in the livestream feed to count and identify the number of pills on-the-fly. In some implementations, the image analysis engine 410 may include a data feed from the enterprise pharmacy data systems 420 to the prescription validator 414 to support counting and differentiation of pills identified in the images.

In some implementations, the dispensing application 434 coordinates with the verification workflow 436 to generate workflow interfaces to implement an end-to-end prescription fill process. The following figures include a variety of screen shots of an example dispensing application 434 on a pharmacy computing device 432 used to implement an end-to-end prescription fill process.

Figure 12B:
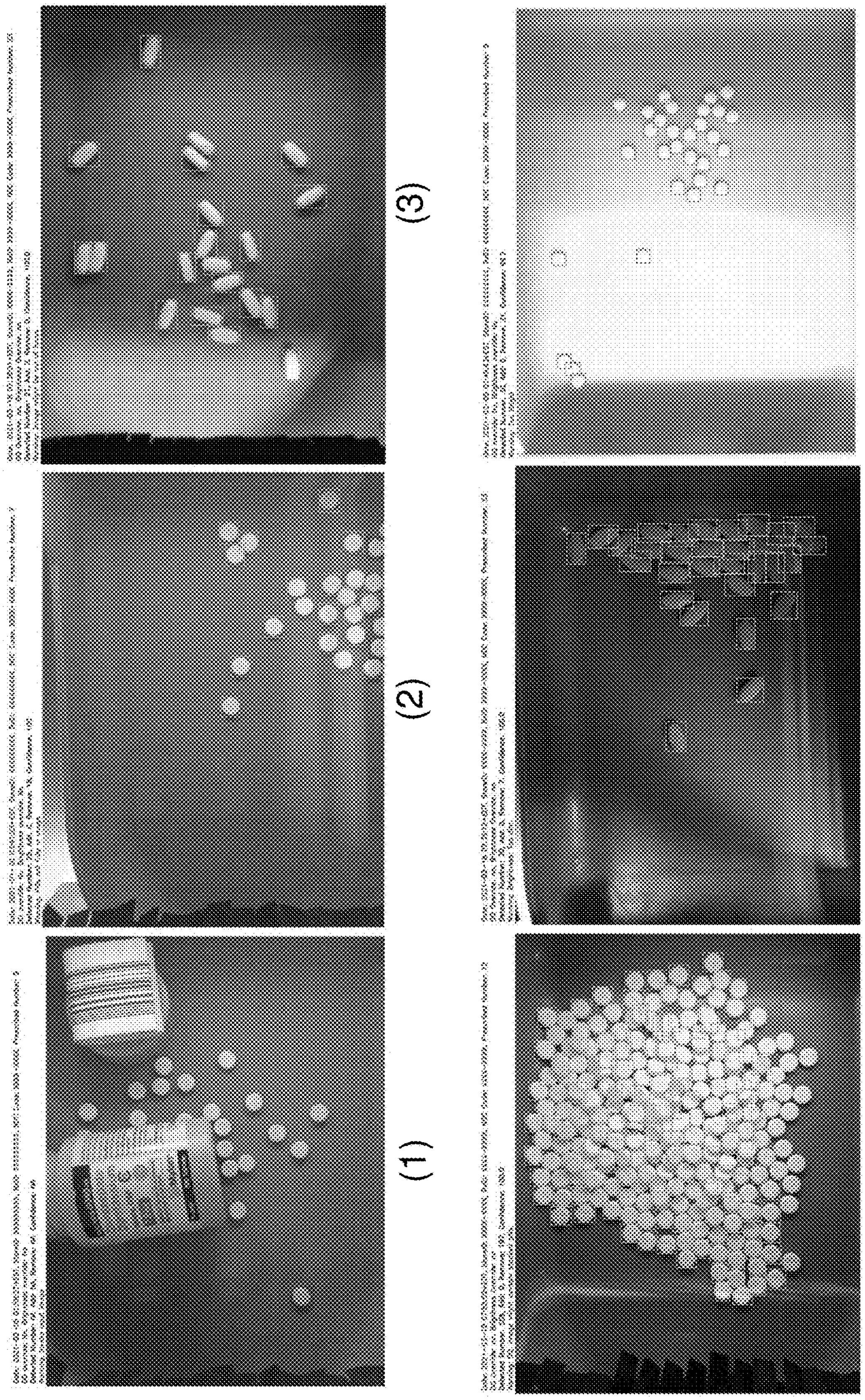
FIG. 12B shows a graphical representation of sample captured images with various identified warning conditions.

FIG. 12B illustrates various views including captured images of the prescription product in the field of view of the camera of the imaging device. Illustrated is an AI annotation of captured images with various image quality alerts notifying, for example, a technician or pharmacist of an issue that impacting the ability of the model to accurately assess the image. The various views (1)-(6) of FIG. 12B include example images that generated various alerts 908 of FIG. 9B with respect to quality checks of the images. In view (1), the image is rejected with an alert (e.g., warning) generated because other artifacts (e.g., pill bottle, lid, instructions) beyond those elements identified as prescription product are present within the field of view. In view (2), the image is rejected with an alert (e.g., warning) generated because the elements of the prescription product are not entirely within the field of view, as noted by the different highlighting associated with the presence of partial pills at the edge of the image. In view (3), the image is rejected with an alert (e.g., warning) generated because the image is out of focus. In view (4), the image is rejected with an alert (e.g., warning) generated because the image includes prescription product that is stacked on each other thereby resulting in the inability to count the individual pills in the prescription product. In view (5), the image is rejected with an alert (e.g., warning) generated because the image is underexposed (e.g., dim) with non-uniform lighting, resulting in the inability to distinguish individual pills in the prescription product. In view (6), the image is rejected with an alert (e.g., warning) generated because the image is overexposed with non-uniform lighting, resulting in the inability to distinguish individual pills in the prescription product. The above alerts relating to image rejections were further described above with respect to FIG. 9B.

Figure 12C:
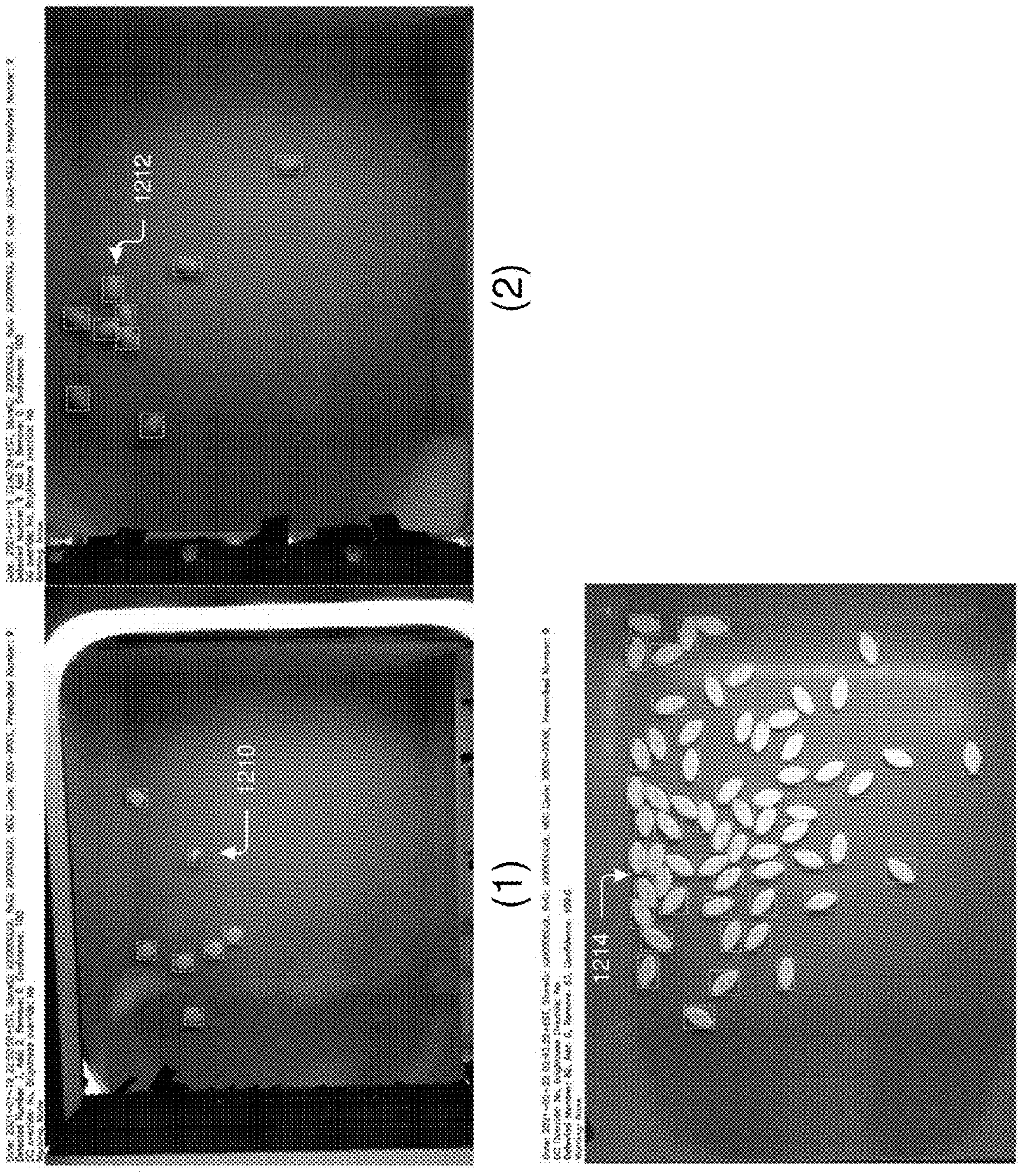
FIG. 12C shows a graphical representation of sample captured images from which electronically generated quantity of pill counts may be generate.

FIG. 12C illustrates various views including captured images of the prescription product in the field of view of the camera of the imaging device. Illustrated is an AI annotation of captured images with dispensed quantity alerts. The various views (1)-(3) of FIG. 12C include example images that were acceptable and did not generate alerts (e.g., warnings) in the check for quality process described above with respect to FIG. 9B. In view (1), the quality of the image is acceptable and results in resolution of each of the pills in the field of view. The dispensed quantity is less than the target or prescribed quantity. Specifically, a pill 1210 that is located on its edge is still resolved and included in the count of the pills in the prescription product. In view (2), the quality of the image is acceptable and results in resolution of each of the pills in the field of view. The dispensed quantity is a sufficient quantity in relation to the target or prescribed quantity. Specifically, a cluster 1212 of pills is still resolved and all are included in the count of the pills in the prescription product. In view (3), the quality of the image is acceptable and results in resolution of each of the pills in the field of view. The dispensed quantity is greater than the target or prescribed quantity. Specifically, pills that are touching a cluster 1214 are still resolved and all are included in the count of the pills in the prescription product.

Figure 13A:
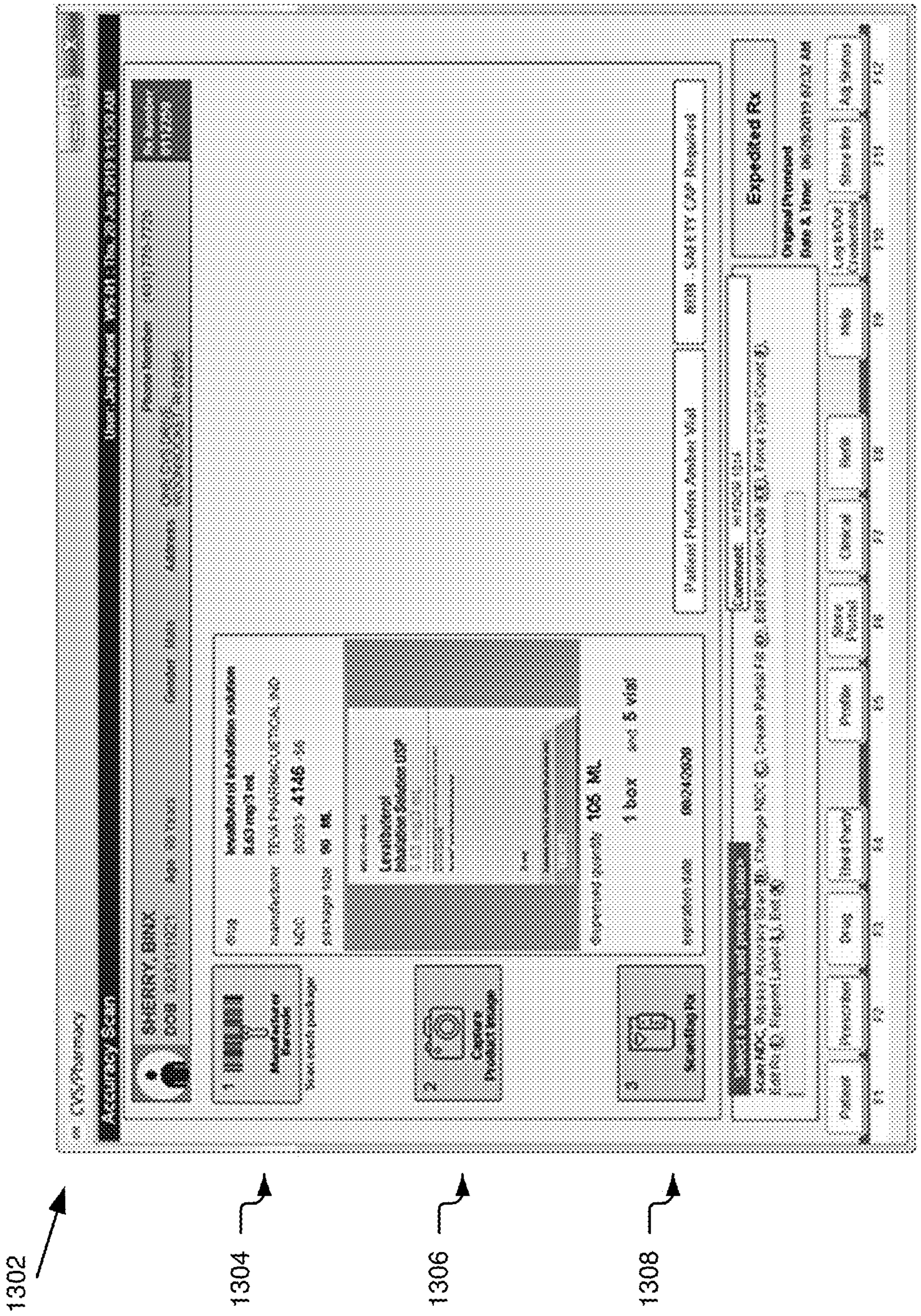
FIGS. 13A-13E are graphical representations of an example user interfaces generated by a dispensing application in accordance with the present disclosure.

FIG. 13A shows an example user interface generated by a dispensing application 434. FIG. 13A shows an example starting page 1302 in the prescription fill process. After printing the prescription label and accompanying documents, the technician may be led through a series of interfaces configured by the workflow to successfully complete three steps to qualify the prescription to be virtually verified by a pharmacist using the images. The first step 1304 is to scan the barcode of each package to validate the right prescription product. The second step 1306 is to capture one or more images of the prescription product. The third step 1308 is to scan and bag the prescription product for pick-up. In FIG. 13A, the technician starts by performing a scan of z, NDC, expiration date, etc. to validate the prescription product in the received images.

Figure 13B:
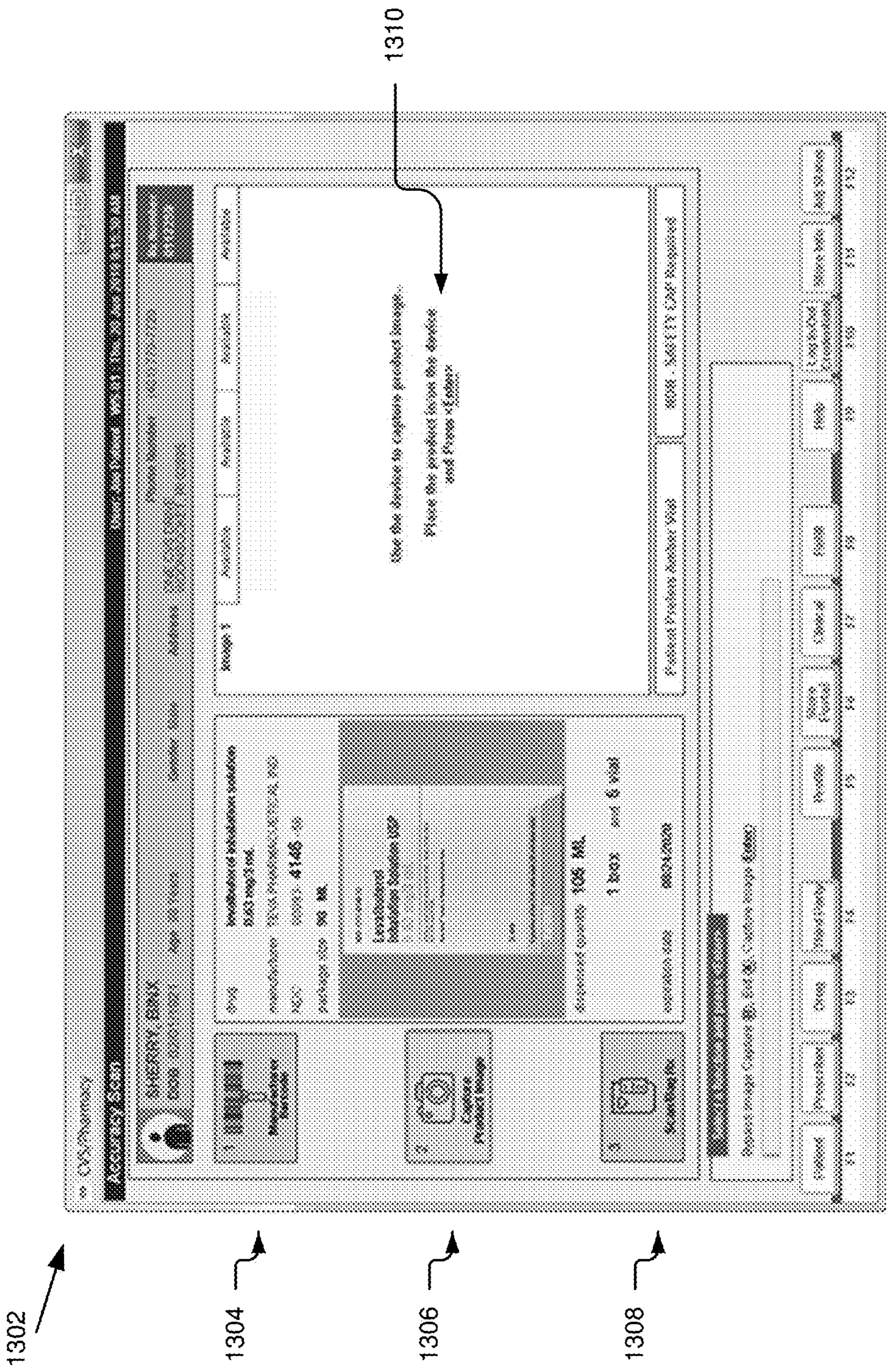

After completing the appropriate product scans, the interface in the verification workflow shown in FIG. 13B shifts to the second step 1306 of capturing images of the prescription product using the imaging device. The capture image portion of the interface in FIG. 13B includes instructions 1310 for the technician to place the product in the imaging device to capture images. The technician may place the product in the imaging device and select 'Enter' option in the interface to start capturing one or more images of the product. In some implementations, the user will be able to view a livestream camera feed on-screen to help guide the camera to aim and focus on product placement.

Figure 13C:
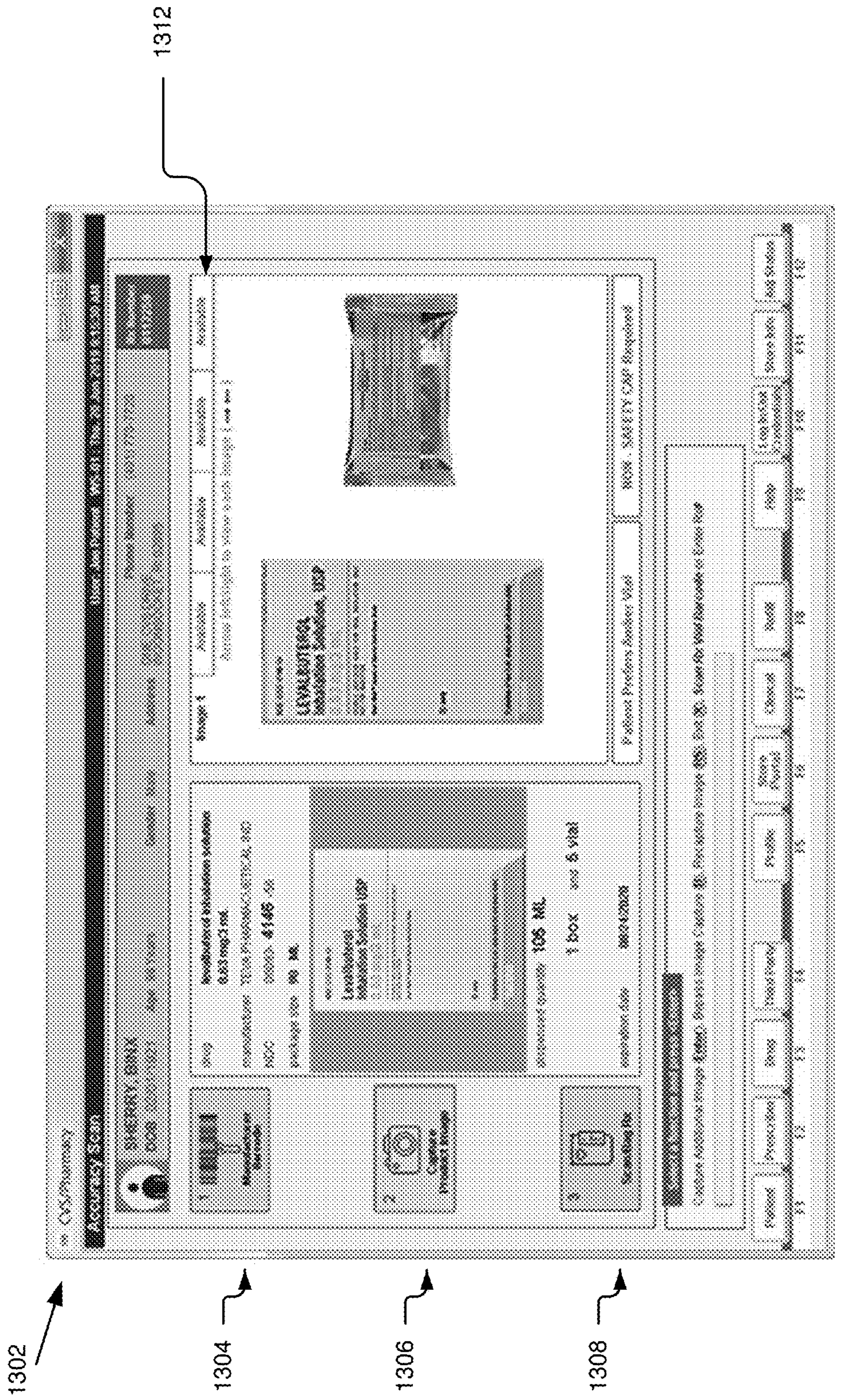

As shown in the interface of FIG. 13C, the technician may capture more than one image and build an album of images for the pharmacist to review during virtual verification. In one specific implementation, the technician may capture 15 or more images. The interface displays each of the captured images in a separate tab 1312. The technician may also use menu options included in the interface, such as recapture image, bypass image capture, delete, and exit to manage the creation of the album of images.

Figure 13D:
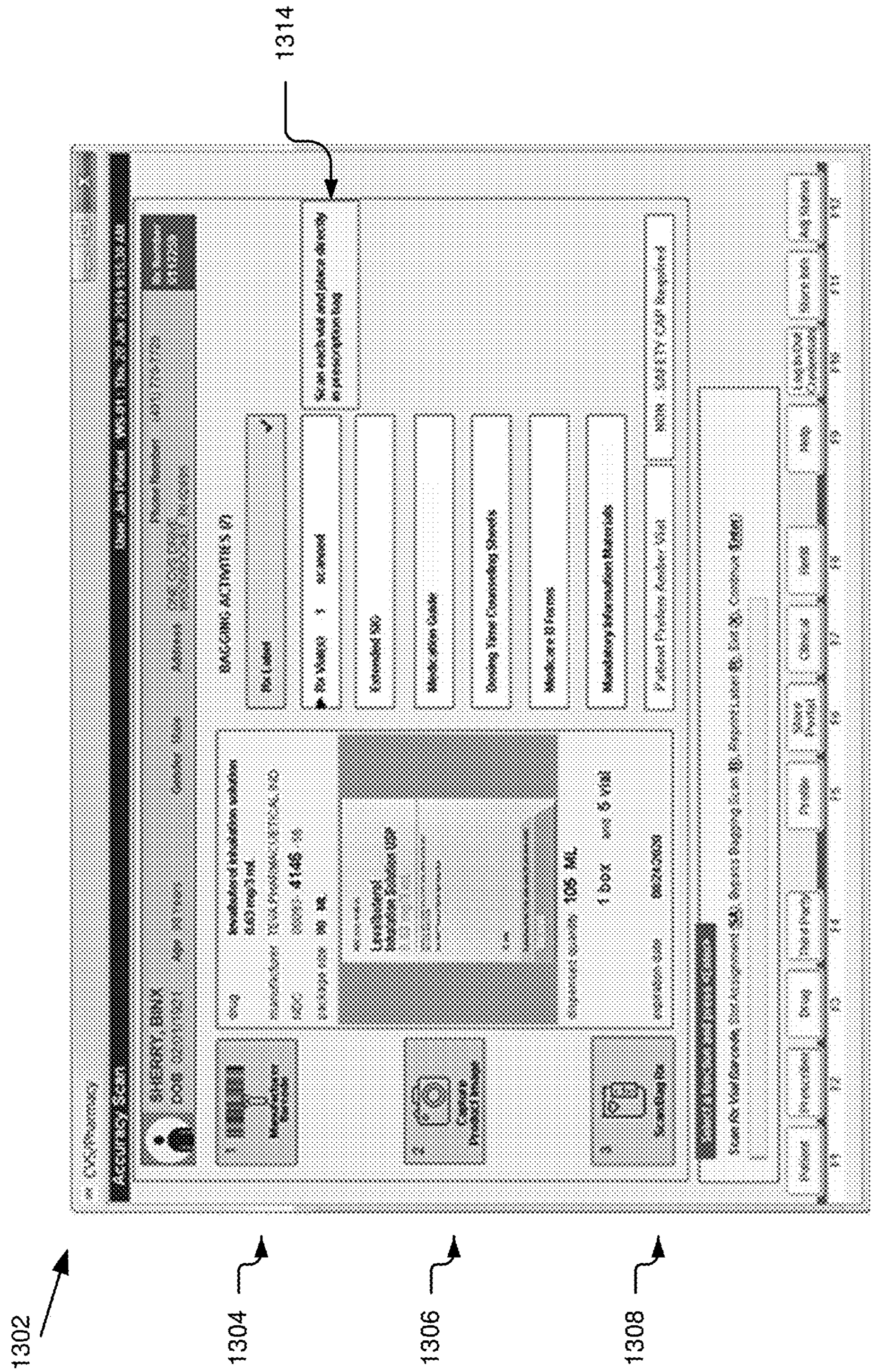
Figure 13E:
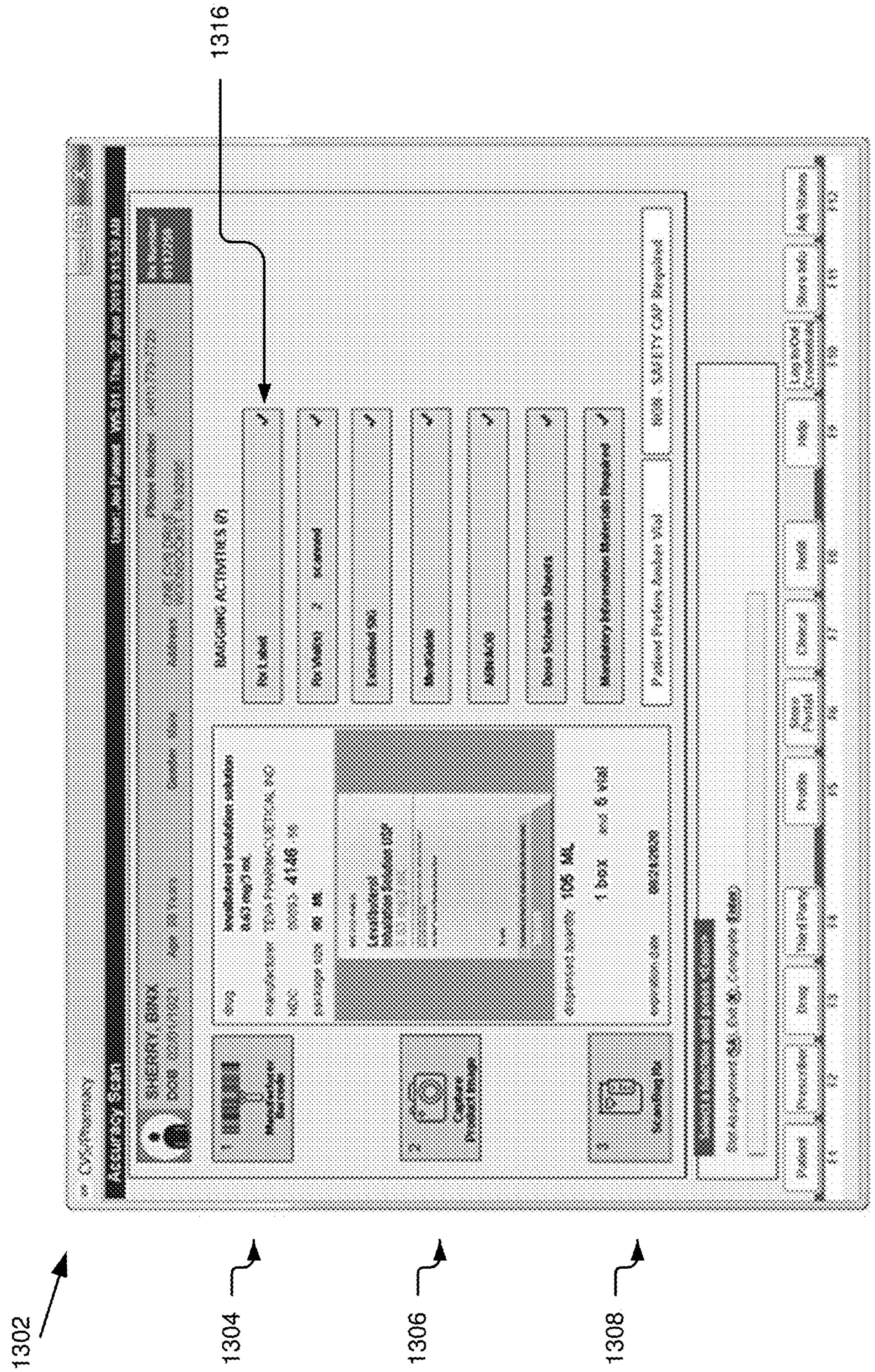

After capturing the images of the prescription product, the interface in the workflow shown in FIG. 13D brings the technician to the third step of guided bagging process 1314 to complete the prescription fill. The interface in FIG. 13D includes a dynamic list of bagging activities that the technician has to complete for each prescription fill. Some of the activities relate to FDA/Medicare documents. Some of the other activities are for internal auditing of the pharmacy. The activities include but not limited to:

1—Scanning the prescription label
2—Scanning and bagging the prescription vials/products in a prescription bag
3—Scanning & attaching Extended SIG (directions)
4—Scanning & attaching Medication guide
5—Scanning & attaching Medicare B forms
6—Scanning & attaching Dosing Time Counseling Sheets
7—Confirming Mandatory Information Materials inclusion As each activity is completed, the interface shown in FIG. 13E lets the technician visually check off 1316 each of the activities by progressing through the workflow. Once the list of bagging activities is complete, the technician may complete his or her workflow and physically transfer the prescription package or bag to the waiting bin for hold. The prescription package cannot be sold to the customer without the pharmacist completing the verification workflow.

Figure 14:
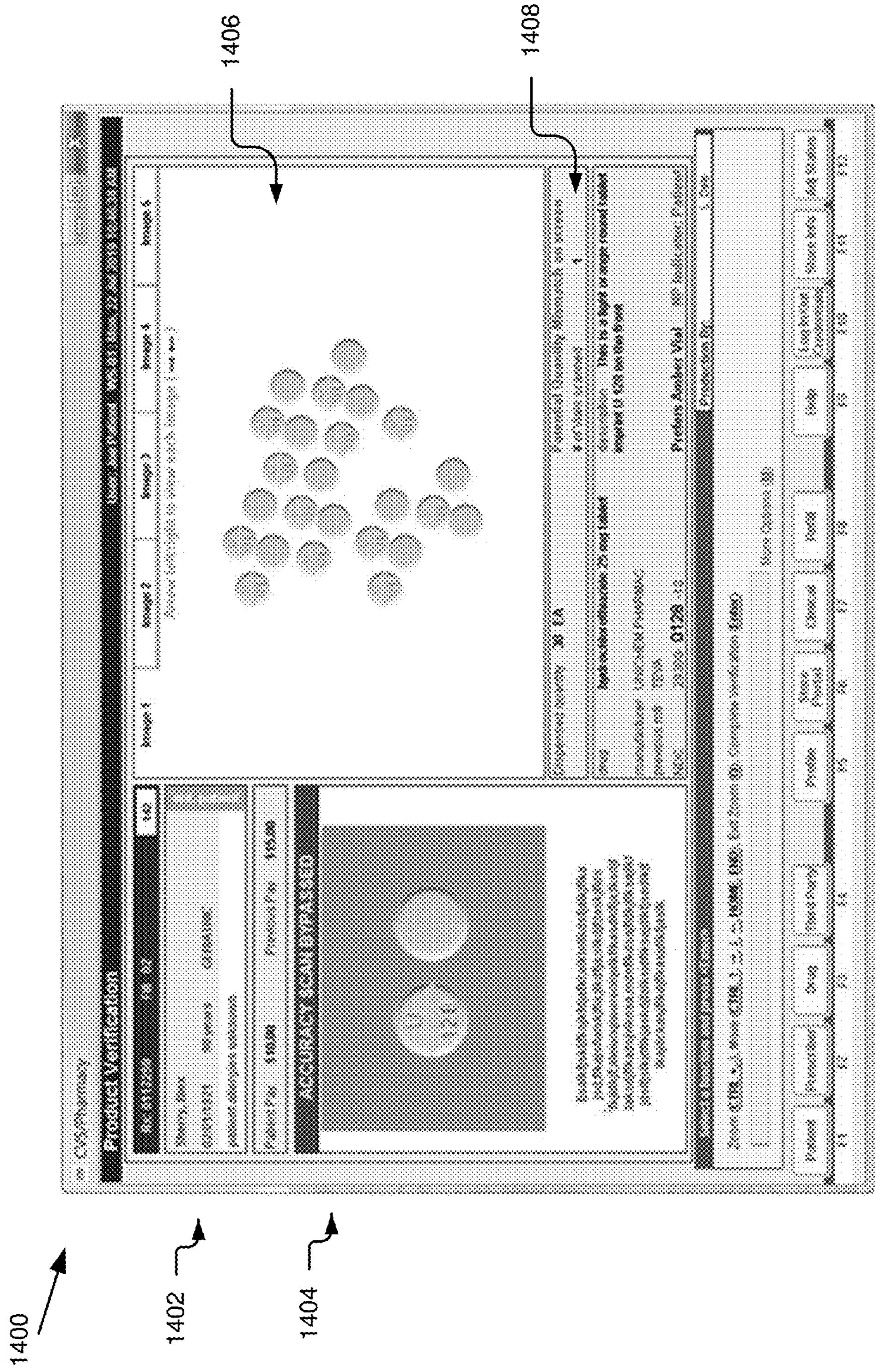
FIG. 14 is a graphical representation of an example user interface for visual verification of the prescription product.

FIG. 14 shows an example interface 1400 in the virtual verification of the prescription product. The interface 1400 in FIG. 14 highlights all relevant information for the pharmacist to review and verify. For example, the interface may include patient details 1402 including name, age, classification, and allergies. The interface may highlight any step 1404 in the prescription fill process that was bypassed or done incorrectly by the technician. The pharmacist may review the reason for the bypassed step if provided by the technician. The interface may allow the pharmacist to review each of the images 1406 analyzed and returned by the image analysis engine. The pharmacist may only complete verification after reviewing each image in the album. The image analysis engine may flag one or more images for any detected anomalies and provide an appropriate reasoning for the flagging. In the example of FIG. 14, the interface highlights 1408 that there is a potential mismatch between the dispensed quantity and the actual count of the pills in the captured image. In another example, the interface may identify the type of pills in the captured image and highlight presence of an unrelated pill mixed in with the prescribed pills. In some implementations, the interface may allow the pharmacist to access the stock images of the imaged pills from the enterprise pharmacy data system to perform a comparison. If the comparison check passes, the pharmacist may complete virtual verification and approve the prescription fill for customer pick-up. If the comparison check fails, the pharmacist may reject the prescription fill and provide comment indicating the reason for rejection. The prescription may be refilled by the technician or the pharmacist depending on the pharmacy workflow.

Figure 15:
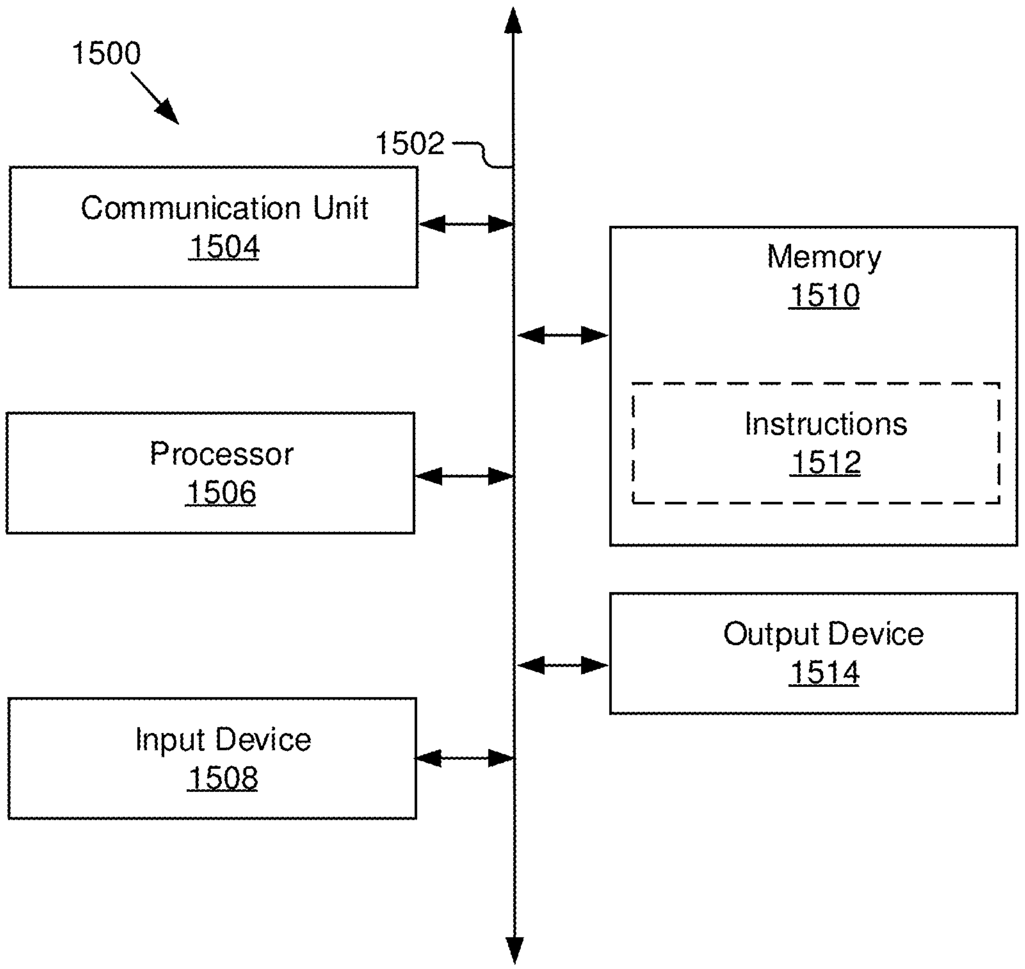
FIG. 15 is a block diagram of an example pharmacy computing device and servers hosting enterprise pharmacy data systems and/or the image analysis engine.

FIG. 15 is a block diagram of an example computing device 1500, which may represent the computer architecture of a pharmacy computing device and servers hosting enterprise pharmacy data systems and/or the image analysis engine. As depicted, the computing device 1500 may include a processor 1506, a memory 1510, a communication unit 1504, an input device 1508, and an output device 1514, which may be communicatively coupled by a bus 1502. The computing device 1500 depicted in FIG. 15 is provided by way of example and it should be understood that it may take other forms and include additional or fewer components without departing from the scope of the present disclosure. For instance, various components of the computing device 1500 may be coupled for communication using a variety of communication protocols and/or technologies including, for instance, communication buses, software communication mechanisms, computer networks, etc. While not shown, the computing device 1500 may include various operating systems, sensors, additional processors, and other physical configurations. The processor 1506, memory 1510, communication unit 1504, etc., are representative of one or more of these components. The processor 1506 may execute software instructions by performing various input, logical, and/or mathematical operations. The processor 1506 may have various computing architectures to process data signals (e.g., CISC, RISC, etc.).

The processor 1506 may be physical and/or virtual and may include a single core or plurality of processing units and/or cores. In some implementations, the processor 1506 may be coupled to the memory 1510 via the bus 1502 to access data and instructions therefrom and store data therein. The bus 1502 may couple the processor 1506 to the other components of the computing device 1500 including, for example, the memory 1510, the communication unit 1504, the input device 1508, and the output device 1514. The memory 1510 may store and provide access to data to the other components of the computing device 1500. The memory 1510 may be included in a single computing device or a plurality of computing devices. In some implementations, the memory 1510 may store instructions and/or data that may be executed by the processor 1506. For example, the memory 1510 may store one or more of the image analysis engines, dispensing application, workflow systems, pharmacy services, verification workflow etc. and their respective components, depending on the configuration. The memory 1510 is also capable of storing other instructions and data, including, for example, an operating system, hardware drivers, other software applications, databases, etc. The memory 1510 may be coupled to the bus 1502 for communication with the processor 1506 and the other components of computing device 1500.

The memory 1510 may include a non-transitory computer-usable (e.g., readable, writeable, etc.) medium, which can be any non-transitory apparatus or device that can contain, store, communicate, propagate, or transport instructions 1512, data, computer programs, software, code, routines, etc., for processing by or in connection with the processor 1506. In some implementations, the memory 1510 may include one or more of volatile memory and non-volatile memory (e.g., RAM, ROM, hard disk, optical disk, etc.). It should be understood that the memory 1510 may be a single device or may include multiple types of devices and configurations.

The bus 1502 can include a communication bus for transferring data between components of a computing device or between computing devices, a network bus system including the network 1502 or portions thereof, a processor mesh, a combination thereof, etc. In some implementations, the various components of the computing device 1500 cooperate and communicate via a communication mechanism included in or implemented in association with the bus 1502. In some implementations, bus 1502 may be a software communication mechanism including and/or facilitating, for example, inter-method communication, local function or procedure calls, remote procedure calls, an object broker (e.g., CORBA), direct socket communication (e.g., TCP/IP sockets) among software modules, UDP broadcasts and receipts, HTTP connections, etc. Further, communication between components of computing device 1500 via bus 1502 may be secure (e.g., SSH, HTTPS, etc.).

The communication unit 1504 may include one or more interface devices (I/F) for wired and/or wireless connectivity among the components of the computing device 1500. For instance, the communication unit 1504 may include, but is not limited to, various types of known connectivity and interface options. The communication unit 1504 may be coupled to the other components of the computing device 1500 via the bus 1502. The communication unit 1504 can provide other connections to the network and to other entities of the system in FIG. 4 using various standard communication protocols.

The input device 1508 may include any device for inputting information into the computing device 1500. In some implementations, the input device 1508 may include one or more peripheral devices. For example, the input device 1508 may include a keyboard, a pointing device, microphone, an image/video capture device (e.g., camera), a touchscreen display integrated with the output device 1514, etc. The output device 1514 may be any device capable of outputting information from the computing device 1500. The output device 1514 may include one or more of a display (LCD, OLED, etc.), a printer, a 3D printer, a haptic device, audio reproduction device, touch-screen display, a remote computing device, etc. In some implementations, the output device 1514 is a display which may display electronic images and data output by a processor, such as processor 1506 of the computing device 1500 for presentation to a user.

Figure 16:
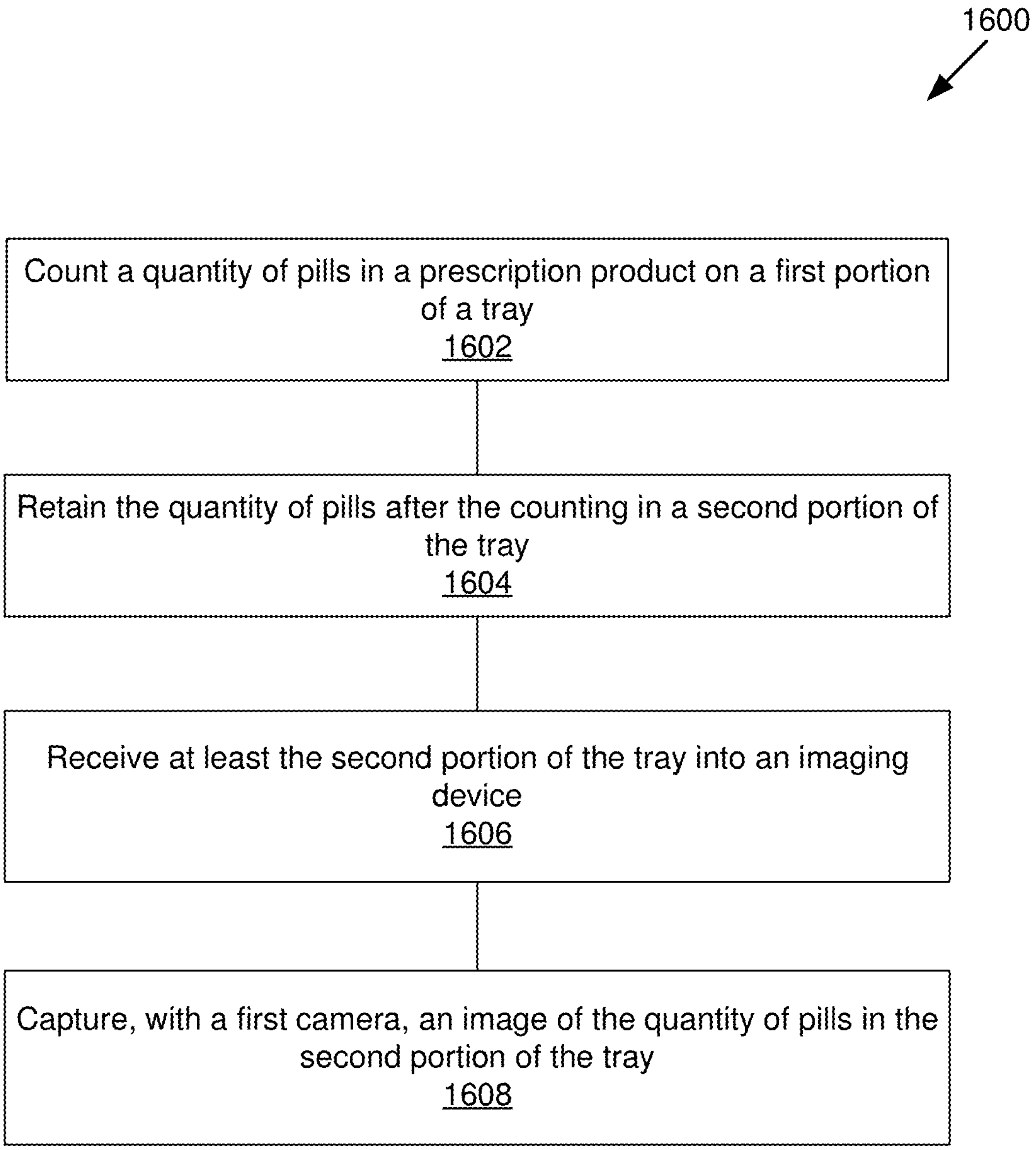
FIG. 16 is a flowchart of configuring a system for facilitating virtual verification of dispensed prescription product.

FIG. 16 is a flowchart 1600 for configuring a system for facilitating virtual verification of dispensed prescription product.

In a block 1602, a quantity of pills in a prescription product is counted on a first portion of a tray. In one example, the quantity of pills may be retrieved from a bulk container. In another example, the quantity of pills may be retrieved by an automated process. In other examples, the quantity of pills may be retrieved and counted by a technician.

In a block 1604, the quantity of pills may be retained after the counting in a second portion of the tray. In one example, the second portion of the tray is a lower portion of a counting tray, such as a CAIT described herein. In another example, the second portion of the tray biases the quantity of pills toward a field of view of the first camera.

In a block 1606, at least the second portion of the tray is received in an imaging device. In one example, at least a portion of the second portion is aligned within the field of view of a first camera of the imaging device. In another example, the second portion of the tray is positioned opposite the first camera and is positioned in the field of view of the first camera. In other examples, the second portion of the tray is illuminated when the second portion of the tray is received in the imaging device.

In a block 1608, a first camera captures an image of the quantity of pills in the second portion of the tray. In one example, the images may be stored and made available for access and verification by a pharmacist.

Figure 17:
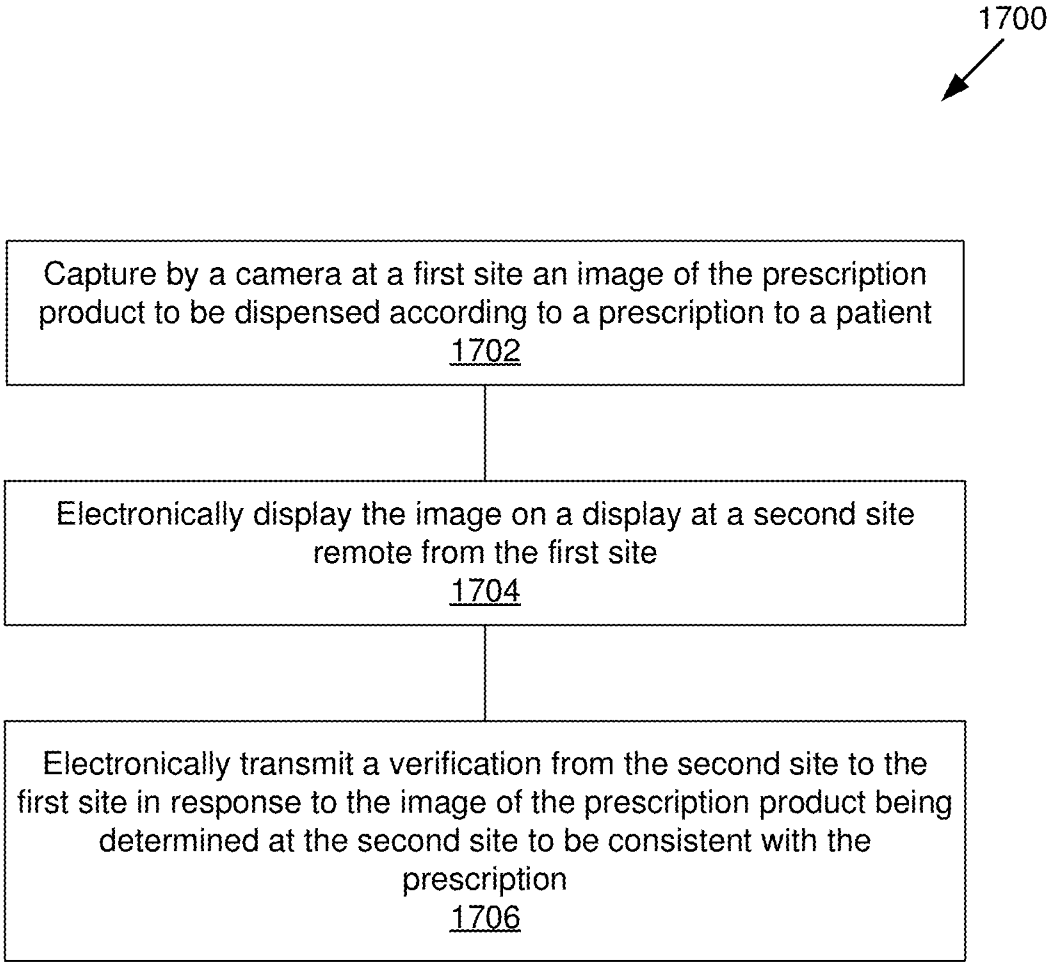
FIG. 17 is a flowchart for a method for virtual verification of dispensed prescription product.

FIG. 17 is a flowchart 1700 for a method for virtual verification of dispensed prescription product.

In a block 1702, an image of the prescription product to be dispensed according to a prescription to a patient is captured by a camera at a first site. In one example, the camera may be configured with an imaging device as described herein. In another example, a quality of the image is determined based on at least one of a presence of expected features and absence of unexpected features of the prescription product in the image, and another image is recaptured to replace the image in response to the quality being unacceptable. In other examples, the quality of the image at the first site is determined based on a brightness of the image, and another image is recaptured to replace the image in response to the quality being unacceptable. In other examples, an electronically determined quantity of pills from the image is electronically counted at the first site. In other examples, a confidence factor is electronically generated at the first site based on the electronically determined quantity of pills. In still other examples, each of the electronically determined quantity of pills is annotated in response to completion of the electronically counting each of the electronically determined quantity of pills in the prescription product. In yet further examples, ones of the prescription product that are unable to be electronically counted are differently annotated. In further examples, the electronically determined quantity of pills and the confidence factor of the electronically determined quantity of pills is associated with the image of the prescription product.

In a block 1704, the image is electronically displayed on a display at a second site remote or physically distanced/separated from the first site. In one example, the second site includes a pharmacist for verifying the dispensed prescription product.

In a block 1706, a verification is electronically transmitted from the second site to the first site in response to the image of the prescription product being determined at the second site to be consistent with the prescription. In one example, the first site and the second site are spatially distant. In another example, the first site and the second site are collocated but separately manned. In yet another example, the prescription product is packaged for sale at the first site prior to receiving the verification from the second site.

While the examples provided have been in the context of a retail pharmacy, other applications of the described systems and methods are also possible. For example, workstation allocation and related task management could be applied to retail store (or pharmacy "front store") operations or retail clinic operations. Other applications may include mail order pharmacies, long term care pharmacies, etc.

While at least one example implementation has been presented in the foregoing detailed description of the technology, it should be appreciated that a vast number of variations may exist. It should also be appreciated that an exemplary implementation or exemplary implementations are examples, and are not intended to limit the scope, applicability, or configuration of the technology in any way. Rather, the foregoing detailed description will provide those skilled in the art with a convenient road map for implementing an example implementation of the technology, it being understood that various modifications may be made in a function and/or arrangement of elements described in an exemplary implementation without departing from the scope of the technology, as set forth in the appended claims and their legal equivalents.

As will be appreciated by one of ordinary skill in the art, various aspects of the present technology may be embodied as a system, method, or computer program product. Accordingly, some aspects of the present technology may take the form of an entirely hardware implementation, an entirely software implementation (including firmware, resident software, micro-code, etc.), or a combination of hardware and software aspects that may all generally be referred to herein as a circuit, module, system, and/or network. Furthermore, various aspects of the present technology may take the form of a computer program product embodied in one or more computer-readable mediums including computer-readable program code embodied thereon.

Any combination of one or more computer-readable mediums may be utilized. A computer-readable medium may be a computer-readable signal medium or a physical computer-readable storage medium. A physical computer readable storage medium may be, for example, but not limited to, an electronic, magnetic, optical, crystal, polymer, electromagnetic, infrared, or semiconductor system, apparatus, or device, etc., or any suitable combination of the foregoing. Non-limiting examples of a physical computer-readable storage medium may include, but are not limited to, an electrical connection including one or more wires, a portable computer diskette, a hard disk, random access memory (RAM), read-only memory (ROM), an erasable programmable read-only memory (EPROM), an electrically erasable programmable read-only memory (EEPROM), a Flash memory, an optical fiber, a compact disk read-only memory (CD-ROM), an optical processor, a magnetic processor, etc., or any suitable combination of the foregoing. In the context of this document, a computer-readable storage medium may be any tangible medium that can contain or store a program or data for use by or in connection with an instruction execution system, apparatus, and/or device.

Computer code embodied on a computer-readable medium may be transmitted using any appropriate medium, including but not limited to, wireless, wired, optical fiber cable, radio frequency (RF), etc., or any suitable combination of the foregoing. Computer code for carrying out operations for aspects of the present technology may be written in any static language, such as the C programming language or other similar programming language. The computer code may execute entirely on a user's computing device, partly on a user's computing device, as a stand-alone software package, partly on a user's computing device and partly on a remote computing device, or entirely on the remote computing device or a server. In the latter scenario, a remote computing device may be connected to a user's computing device through any type of network, or communication system, including, but not limited to, a local area network (LAN) or a wide area network (WAN), Converged Network, or the connection may be made to an external computer (e.g., through the Internet using an Internet Service Provider).

Various aspects of the present technology may be described above with reference to flowchart illustrations and/or block diagrams of methods, apparatus, systems, and computer program products. It will be understood that each block of a flowchart illustration and/or a block diagram, and combinations of blocks in a flowchart illustration and/or block diagram, can be implemented by computer program instructions. These computer program instructions may be provided to a processing device (processor) of a general-purpose computer, special purpose computer, or other programmable data processing apparatus to produce a machine, such that the instructions, which can execute via the processing device or other programmable data processing apparatus, create means for implementing the operations/acts specified in a flowchart and/or block(s) of a block diagram.

Some computer program instructions may also be stored in a computer-readable medium that can direct a computer, other programmable data processing apparatus, or other device(s) to operate in a particular manner, such that the instructions stored in a computer-readable medium to produce an article of manufacture including instructions that implement the operation/act specified in a flowchart and/or block(s) of a block diagram. Some computer program instructions may also be loaded onto a computing device, other programmable data processing apparatus, or other device(s) to cause a series of operational steps to be performed on the computing device, other programmable apparatus or other device(s) to produce a computer-implemented process such that the instructions executed by the computer or other programmable apparatus provide one or more processes for implementing the operation(s)/act(s) specified in a flowchart and/or block(s) of a block diagram.

A flowchart and/or block diagram in the above figures may illustrate an architecture, functionality, and/or operation of possible implementations of apparatus, systems, methods, and/or computer program products according to various aspects of the present technology. In this regard, a block in a flowchart or block diagram may represent a module, segment, or portion of code, which may comprise one or more executable instructions for implementing one or more specified logical functions. It should also be noted that, in some alternative aspects, some functions noted in a block may occur out of an order noted in the figures. For example, two blocks shown in succession may, in fact, be executed substantially concurrently, or blocks may at times be executed in a reverse order, depending upon the operations involved. It will also be noted that a block of a block diagram and/or flowchart illustration or a combination of blocks in a block diagram and/or flowchart illustration, can be implemented by special purpose hardware-based systems that may perform one or more specified operations or acts, or combinations of special purpose hardware and computer instructions.

While one or more aspects of the present technology have been illustrated and discussed in detail, one of ordinary skill in the art will appreciate that modifications and/or adaptations to the various aspects may be made without departing from the scope of the present technology, as set forth in the following claims.

What is claimed is:

1. A tray comprising:

a first portion for receiving a quantity of pills in a prescription;

a first spout positioned on a periphery of the first portion for returning an excess amount of pills to a storage container;

a second portion for imaging the quantity of pills in the prescription, wherein the entire second portion comprises a field of view area for a camera; and a second spout positioned on a periphery of the second portion for dispensing the quantity of pills into a sales container, wherein the first portion and the second portion are connected so that the quantity of pills can be slid from the first portion to the second portion.

2. The tray of claim 1, wherein:

the second portion further comprises an imaging area; and the imaging area is configured to maintain a constant distance from an imaging device.

3. The tray of claim 2, wherein the second portion further comprises at least one slope to bias the quantity of pills toward the imaging area.

4. The tray of claim 3, further comprising at least four slopes to bias the quantity of pills toward the imaging area.

5. The tray of claim 1, wherein the second portion is lower than the first portion while the tray is placed on a flat surface.

6. The tray of claim 1, wherein the first portion and the second portion are divided by a physical barrier which allows the quantity of pills to be moved from the first portion to the second portion while preventing the quantity of pills from being moved from the second portion to the first portion.

7. The tray of claim 1, wherein:

the first portion comprises at least four sides;

a first side and a second side of the at least four sides comprise two sidewall portions;

the two sidewall portions are connected to the first spout;

a third side of the at least four sides is connected to the second portion; and a fourth side of the at least four sides is open to permit access to the first portion for sliding the quantity of pills from the first portion to the second portion.

8. The tray of claim 1, wherein the second spout further comprises a top cap to assist in keeping the quantity of pills from spilling when the quantity of pills is being dispensed into the sales container.

9. The tray of claim 1, wherein the second portion further comprises walls around the periphery of the second portion.

10. The tray of claim 1, wherein the tray is configured to be inserted in an imaging device and, when inserted in the imaging device:

the first portion is disposed outside the imaging device;

the second portion is disposed inside the imaging device; and the second portion is positioned in a field of view of the camera in the imaging device.

11. A tray comprising:

a first portion configured to manually receive a quantity of pills in a prescription;

a first spout positioned on a periphery of the first portion and configured for returning an excess quantity of pills to a storage container;

a second portion configured to receive the quantity of pills from the first portion, wherein the entire second portion comprises an imaging area configured to be in a field of view of a camera when the tray is inserted in an imaging device;

a second spout positioned on the periphery of the second portion for dispensing the quantity of pills into a sales container; and a physical barrier connecting the first portion and the second portion and selectively allowing the quantity of pills to be slid from the first portion to the second portion.

12. The tray of claim 11, wherein the second portion further comprises at least one slope to bias the quantity of pills toward the imaging area.

13. The tray of claim 12, further comprising at least four slopes to bias the quantity of pills toward the imaging area.

14. The tray of claim 11, wherein the physical barrier comprises:

a step that positions the first portion higher than the second portion; and an opening at a top of the step to allow the quantity of pills to be moved from the first portion to the second portion.

15. The tray of claim 11, wherein the second portion is lower than the first portion while the tray is placed on a flat surface.

16. The tray of claim 15, wherein the first portion is supported by at least one leg while the tray is placed on the flat surface.

17. The tray of claim 11, wherein:

the first portion comprises at least four sides;

a first side and a second side of the at least four sides comprise two sidewall portions;

the two sidewall portions are connected to the first spout;

a third side of the at least four sides is connected to the second portion; and a fourth side of the at least four sides is open to permit access to the first portion for sliding the quantity of pills from the first portion to the second portion.

18. The tray of claim 11, wherein, when the tray is inserted in the imaging device:

the first portion is disposed outside the imaging device;

the second portion is disposed inside the imaging device; and the second portion is positioned in the field of view of the camera in the imaging device.

19. A method for preparing a prescription for sale, the method comprising:

adding a quantity of pills in a prescription to a first portion of a tray;

manually counting the quantity of pills to determine a second quantity of pills;

returning an excess quantity of pills to a storage container through a first spout positioned on a periphery of the first portion;

sliding the second quantity of pills from the first portion to a second portion;

capturing, by a camera, an image of the second quantity of pills on the second portion, wherein the entire second portion comprises a field of view area for capturing the image by the camera;

transmitting the captured image to a remote location; and dispensing, responsive to verification, at the remote location, of a medication type and the second quantity of pills in the image being consistent with the prescription, the second quantity of pills through a second spout positioned on a periphery of the second portion into a sales container.

20. The method of claim 19, further comprising:

inserting, prior to imaging the second quantity of pills, the tray into an imaging device comprising the camera and configured to generate the image, wherein:

the second portion is lower than the first portion while the tray is placed on a flat surface; and sliding the second quantity of pills from the first portion to the second portion comprises sliding the second quantity of pills down a step between the first portion and the second portion.

21. The method of claim 19, wherein capturing the image uses the camera at a first site and further comprising:

electronically displaying the image on a display at a second site remote from the first site; and electronically transmitting a verification from the second site to the first site in response to the image of the second quantity of pills being determined at the second site to be consistent with the prescription.

* * * * *